(12) United States Patent
Larson et al.

(10) Patent No.: US 7,449,682 B2
(45) Date of Patent: Nov. 11, 2008

(54) SYSTEM AND METHOD FOR DEPTH PROFILING AND CHARACTERIZATION OF THIN FILMS

(75) Inventors: Paul E. Larson, Bloomington, MN (US); John F. Moulder, Bloomington, MN (US); David G. Watson, Eden Prairie, MN (US); David S. Perloff, Los Altos Hills, CA (US)

(73) Assignee: Revera Incorporated, Sunnyvale, CA (US)

( * ) Notice: Subject to any disclaimer, the term of this patent is extended or adjusted under 35 U.S.C. 154(b) by 0 days.

(21) Appl. No.: 10/493,492

(22) PCT Filed: Oct. 24, 2002

(86) PCT No.: PCT/US02/34137

§ 371 (c)(1),
(2), (4) Date: Apr. 22, 2004

(87) PCT Pub. No.: WO03/038417

PCT Pub. Date: May 8, 2003

(65) Prior Publication Data

US 2004/0238735 A1 Dec. 2, 2004

Related U.S. Application Data

(63) Continuation-in-part of application No. 10/003,224, filed on Oct. 26, 2001, now abandoned.

(51) Int. Cl.
*H01J 49/00* (2006.01)
(52) U.S. Cl. .......................... 250/281; 250/309; 378/45
(58) Field of Classification Search .................. 250/281
See application file for complete search history.

(56) References Cited

U.S. PATENT DOCUMENTS

| | | | |
|---|---|---|---|
| 3,766,381 A | | 10/1973 | Watson |
| 3,772,522 A | | 11/1973 | Hammond et al. |
| 4,048,498 A | | 9/1977 | Gerlach et al. |
| 4,737,639 A | * | 4/1988 | Rusch ........................ 250/305 |
| 4,810,880 A | | 3/1989 | Gerlach |
| 5,006,706 A | * | 4/1991 | Marcus ....................... 250/288 |
| 5,087,815 A | * | 2/1992 | Schultz et al. .............. 250/309 |
| 5,162,159 A | * | 11/1992 | Tenhover et al. ............ 428/614 |
| 5,280,176 A | * | 1/1994 | Jach et al. .................... 250/305 |
| 5,315,113 A | | 5/1994 | Larson et al. |
| 5,543,648 A | | 8/1996 | Miyawaki |
| 5,579,462 A | * | 11/1996 | Barber et al. ............... 345/440 |
| 5,628,882 A | * | 5/1997 | O'Keefe et al. ........ 204/192.15 |
| 5,888,593 A | * | 3/1999 | Petrmichl et al. ........... 427/563 |
| 5,990,476 A | | 11/1999 | Larson et al. |
| 6,104,029 A | * | 8/2000 | Coxon et al. ................. 250/305 |
| 6,173,036 B1 | * | 1/2001 | Hossain et al. ................ 378/45 |
| 6,259,092 B1 | * | 7/2001 | Brizzolara et al. .......... 250/305 |
| 6,447,891 B1 | * | 9/2002 | Veerasamy et al. .......... 428/216 |

FOREIGN PATENT DOCUMENTS

EP 0 590 308 A2 8/1993
EP 0 594 394 4/1994

OTHER PUBLICATIONS

Briggs, et al., "Pratical Surface Analysis 2$^{nd}$ Ed., vol. 1, Auger and X-ray Photoelectron Spectroscopy," Sec 5.4.2 John Wiley & Sons, Ltd., Chichester 1995; cover page, title pate and 244-248. (6 pgs).
Oswald S, et al.: "XPS Depth Analysis of a Thin Non-Coduction Titanate Superlattice", Mikrochim. ACTA, vol. 133, pp. 303-306, XP002246839.
Gardner S.D. et al.: "Surface Characterization of Carbon Fibers Using Angle-Resolved XPS and ISS". Carbon, Elsevier Science Publishing, New York, NY, US. vol. 33, No. 5, 1995, pp. 587-595, XP004022561, ISSN 0008-6223.
Otte, K., et al.: "XPS and Raman Investigation of Nitrogen Ion Etching for Depth Profiling of CuInSe2 and CuGaSe2", Thins Solid Films, Elsevier-Sequoia S.A. Lausanne, Ch, vol. 361-362, No. 1, Feb. 2000, pp. 498-503. XP004187527.

Kilo, M., et al.: "Reaction Induced Surface Segregation in Amorphous CuZr, NiZr and PdZr Alloys- An XPS and SIMS Depth Profiling Study", Journal of Alloys and Compounds, Elsevier Sequoia, Lausanne, CH., vol. 236, Apr. 1, 1996, pp. 137-150, XP004077212.

International Search Report from PCT/IS02/34137 mailed Oct. 16, 2003, 6 pgs.

"PHI Quantum 2000 Scanning ESCA Microprobe (TM)," Product Information. Physical Electronics, Inc., 1999; 8 pgs.

"Amicus: A High Speed Etching Source—Development and Application," Presented at AVS '99, the 46th Int'l Symposium, Seattle WA., Oct. 26, 1999 [retrieved on Oct. 5, 2001]. Retrieved from the Internet: <URL:http://www.kratoscom/EApps/Kaufmn.html> 5 pgs.

Gibson, et al., "Characterizing Nanometer Oxy-nitride Films with ESCA Low Energy Sputter Depth Profiles," Presented at 15th Int'l Vacuum Congress, AVS 48th Int'l Symposium, 11th Int'l Conference on Solid Surfaces, Oct. 28, 2001, Abst. 1 pg.

Moulder, et al., "Ultra Shallow Depth Profiling by ESCA and SIMS," Presentation at Nat'l Symposium of American Vacuum Society, Baltimore, MD, Nov. 2-6, 1998, 31 pgs.

Principe, et al., "Pushing The Limits of Nitrogen Doped Silicon Oxide Gate Dielectric Materials: The Material Characterization Role of TEM/STEM, PEELS, and XPS" Presented at America Vacuum Society 48th Int'l Symposium, San Francisco CA, 2001, Oct. 28-Nov. 25th, 24 pgs.

* cited by examiner

*Primary Examiner*—David A. Vanore
*Assistant Examiner*—Phillip A. Johnston
(74) *Attorney, Agent, or Firm*—Blakely, Sokoloff, Taylor & Zafman

(57) ABSTRACT

Characterization of a sample, e.g., a depth profile, may be attained using one or more of the following parameters in an electron spectroscopy method or system. The one or more parameters may include using low ion energy ions for removing material from the sample to expose progressively deeper layers of the sample, using an ion beam having a low ion angle to perform such removal of sample material, and/or using an analyzer positioned at a high analyzer angle for receiving photoelectrons escaping from the sample as a result of x-rays irradiating the sample. Further, a correction algorithm may be used to determine the concentration of components (e.g., elements and/or chemical species) versus depth within the sample, e.g., thin film formed on a substrate. Such concentration determination may include calculating the concentration of components (e.g, elements and/or chemical species) at each depth of a depth profile by removing from depth profile data collected at a particular depth (i.e., the depth for which concentration is to be calculated) concentration contributions attributable to deeper depths of the sample. In addition, characterization of a sample, e.g., determination of a component's concentration in a thin film, may be attained by providing calibration information representative of surface spectrum measurements for a plurality of samples correlated with depth profile information for the plurality of samples. At least one characteristic of the sample to be characterized (e.g., concentration of a component) is determined based on one or more surface spectrum measurements for the sample to be characterized and the calibration information.

34 Claims, 15 Drawing Sheets

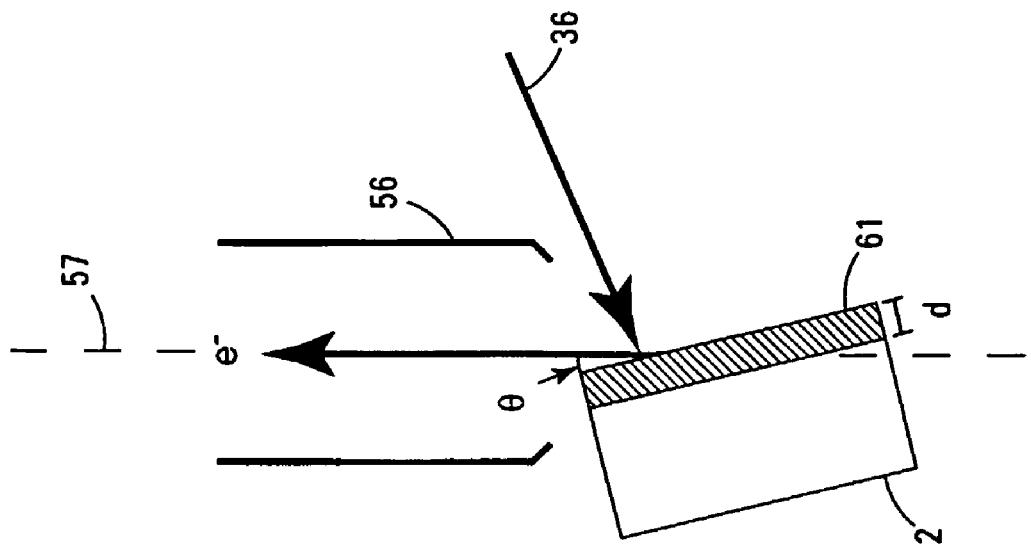
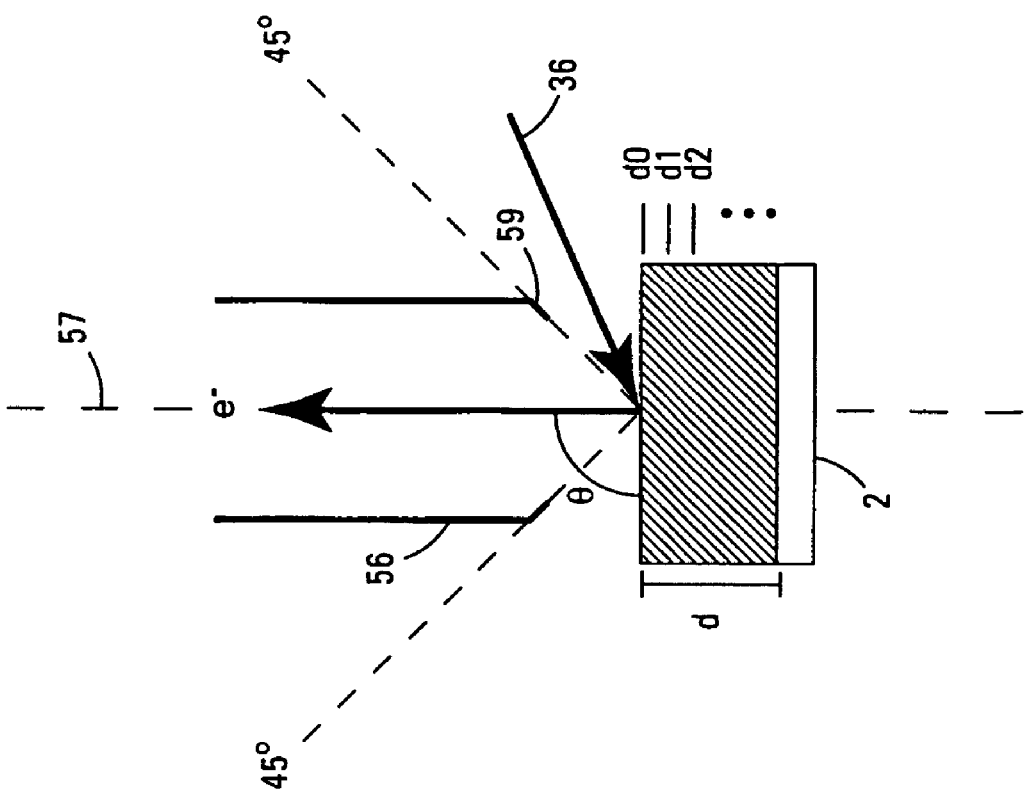

US 7,449,682 B2

SYSTEM AND METHOD FOR DEPTH PROFILING AND CHARACTERIZATION OF THIN FILMS

This application is a U.S. National Stage Patent Application of International PCT patent application No. PCT/US 02/34137, filed 24 Oct. 2002, which claims the benefit of U.S. patent application Ser. No. 10/075,571 (filed 26 Oct. 2001) and U.S. Continuation-in-Part patent application Ser. No. 10/003,224 (filed 26 Oct. 2001) now abandoned, which are incorporated herein by reference in their entirety.

FIELD OF THE INVENTION

The present invention relates to the characterization of samples, e.g., thin films. More particularly, the present invention pertains to the use of depth profiling to characterize samples, and also to non-invasive techniques to characterize samples.

BACKGROUND OF THE INVENTION

Analysis of the composition of a sample (e.g., the element and/or chemical species concentration in a thin film formed on a substrate) is necessary in the manufacture of many different types of devices (e.g., electronic and optical electronic devices). For example, it is necessary to determine the composition of gate oxide films formed in known semiconductor integrated circuit devices, such as processing devices and memory devices. Increases in the density of such devices on an integrated circuit chip and reduction in device dimensions require the advancement of production and characterization technologies of the materials used to fabricate such devices.

For example, recent developments in the fabrication of semiconductor devices may employ shallow implant and/or other ultra-thin structures. In one particular example, gate oxide layers are becoming very thin films, typically less than about 10 nanometers in thickness. Such thin films are difficult to characterize. Such structures will require characterization techniques that have improved sensitivity over conventional characterization techniques. Further, such techniques may also require the characterization to be performed with ample speed.

Various techniques have been used for surface analysis of trace and/or major components in such materials. For example, several of such methods include secondary ion mass spectrometry (SIMS), x-ray photoelectron spectrometry (XPS) (also known as electron spectroscopy for chemical analysis (ESCA)), and Auger electron spectrometry (AES). Such techniques are sensitive to the near-surface region of a material. However, these techniques do permit measurement of material properties as a function of depth beneath the surface through depth profiling.

In typical depth profiling, for example, continuous or periodic ion beam sputtering removes material from the surface of a sample to expose progressively deeper material at one or more various depths of the sample for further measurement and/or analysis. Generally known sputter rates may be used to determine the depth at which the surface measurements are completed. As such, a characterization of the sample as a function of depth beneath the surface can be attained.

However, such techniques and/or the parameters at which such techniques are carried out are inadequate in many respects with regard to characterization of various types of samples and, in particular, for example, with respect to characterization of thin films, e.g., thin gate oxide films. For example, SIMS, which has a very small sampling depth, is used to look for low level dopants and impurities in thin films (e.g., thin films less than 10 nanometers) because of this technique's extreme surface sensitivity. However, SIMS is problematic in that it is difficult to quantify major constituents of a thin film because of matrix effects that impact the secondary ion yield of different chemical species.

Further, AES has also been used for thin film characterization. However, the high intensity electron beam used to make Auger measurements can alter the apparent composition of a thin film by causing chemical damage or the migration of elements within the thin film. For example, nitrogen is known to migrate to the interface of an oxynitride (ONO) film provided on silicon.

XPS, or ESCA, depth profiling has been used for thin film characterization. However, when used, the analyzer of the system is typically positioned at a low analyzer angle relative to the sample surface such that depth resolution is enhanced. Such a low analyzer angle is typically less than 20 degrees. Use of a low analyzer angle generally results in a slow characterization process and also may result in problems associated with placement of the analyzer of the characterization system relative to the sample being analyzed.

Further, ESCA surface measurements taken at various surface to analyzer angles have been used to examine thin films. Such examination has been performed with the use of a mathematical method to obtain depth distributions. However, the mathematical method has no unique solution.

Further, optically based ellipsometry methods have also been used to monitor thin film thickness and composition. However, these methods cannot measure elemental or chemical distributions within the thin film and cannot provide a dose measurement of minor added constituents. In addition, such methods are not capable of providing reliable results for thin films less than 2 nanometers in thickness.

Also, transmission electron microscopy (TEM) combined with electronic energy loss spectroscopy (EELS) measurements can provide thickness and composition distribution information. However, these methods are not practical for process monitoring because of the cost and time needed to prepare samples to be analyzed thereby.

Many of such techniques described above for characterizing thin films are invasive techniques, e.g., they involve destruction of at least one or more portions of the sample. Such techniques, e.g., those that use removal of material during depth profiling, are sufficient in many circumstances, e.g., research and development, product testing, etc., but do not provide for the ability to quickly analyze a thin film such as is necessary in production processes. For example, in such production processes, a thin film being formed typically needs to be analyzed so that such information can be used for production control, product test, etc., without loss of product due to invasive characterization of such films.

For example, nitrogen doped or nitrided silicon oxide is one material that is used as a gate oxide for a transistor gate structure. Such gate structures are only one of the growing number of semiconductor related material systems under development that require characterization at an unprecedented level of complexity. Such challenges are not limited to merely a desire for near-atomic and monolayer spatial resolution, but are magnified by the level of accuracy, precision and speed demanded by the semiconductor fabrication industry. There is a distinctive need to develop adequate characterization methods and systems. The ability to characterize materials at such levels is necessary to enable product development and also necessarily precedes evolution of process control. For example, there is a need for suitable systems and methods to provide parametric thickness, nitrogen dose, and nitrogen distribution information for thin nitrided silicon oxide films such as used for transistor gate oxides.

SUMMARY OF THE INVENTION

Systems and methods according to the present invention for characterizing samples are described herein. In particular, such systems and methods are particularly beneficial for analysis of thin films. As used herein, a thin film is generally defined as being less than about 10 nanometers in thickness. However, the present invention may also be preferably used for films less than about 2 nanometers in thickness.

The present invention provides a more accurate measure of distribution of components (e.g., elements and/or chemical species) within a thin film. Further, depth profiling according to the present invention provides information on film thickness, in addition to the measurement or dose of incorporated components therein.

Generally, the present invention includes the collection of depth profile data using XPS, or ESCA, e.g., depth profile data at various depths of a sample, e.g., a film on a substrate. The depth profile may be accomplished, at least in several embodiments, using one or more of the following parameters in the electron spectroscopy method or system. The one or more parameters may include using low ion energy ions for removing material from the sample to expose progressively deeper layers of the sample, using an ion beam having a low ion angle to perform such removal of sample material, and/or using an analyzer positioned at a high analyzer angle for receiving photoelectrons escaping from the sample as a result of x-rays irradiating the sample.

Further, the present invention also provides a technique to determine the concentration of components (e.g., elements and/or chemical species) versus depth within the sample, e.g., thin film formed on a substrate. In other words, the present invention provides systems and methods for providing a depth profile. In general, the determination of concentration includes calculating the concentration of components (e.g, elements and/or chemical species) at each depth of a depth profile by removing from depth profile data collected at a particular depth (i.e., the depth for which concentration is to be calculated) concentration contributions attributable to deeper depths of the sample based on depth profile data collected at one or more of such deeper depths.

In one method according to the present invention for use in characterizing a sample, depth profile data are collected at each of a plurality of depths of the sample. Each depth corresponds to a sample surface. One or more of the plurality of depths of the sample are provided by removing material from the sample during material removal intervals resulting in sample surfaces at one or more depths of the sample. The depth profile data are collected at each of the plurality of depths of the sample by irradiating the sample with x-rays resulting in the escape of photoelectrons therefrom and detecting photoelectrons escaping from the sample. The photoelectrons are detected by providing an analyzer including an input lens receptive of photoelectrons. The input lens has a central axis extending therethrough. The input lens is positioned such that the central axis of the input lens is at an analyzer angle relative to the sample surface in a range of about 45 degrees to about 90 degrees. A signal representative of the detected photoelectrons is generated. The depth profile data collected for at least a first and second depth is used to characterize the sample at the first depth. The second depth is at a position deeper in the sample than the first depth.

In one embodiment of the method, the second depth is a depth at a sample surface resulting from removal of material from the sample during a material removal interval immediately following collection of depth profile data at the first depth.

In another embodiment of the method, the input lens is receptive to photoelectrons having a photoelectron take-off angle that falls in a cone of +/−20 degrees centered at the analyzer angle.

In yet another embodiment, material is removed from the sample during material removal intervals by sputtering material from the sample using ions having ion energies of less than 500 eV. Further, such removal during the material removal intervals may be provided by sputtering material from a sample surface of the sample using an ion beam provided at an ion angle less than or equal to about 45 degrees relative to the sample surface; more preferably less than or equal to about 20 degrees.

Preferably, the present invention is beneficial in analysis of a sample that includes a thin film having a thickness of less than about 10 nanometers, and even less than about 2 nanometers. For example, the thin film may be a gate dielectric film. Yet further, the depth profile data collected may be used for characterizing composition over a certain thickness of the sample.

Another method according to the present invention for use in characterizing a sample includes collecting depth profile data at each of a plurality of depths of the sample. Each depth has a corresponding sample surface. One or more of the plurality of depths of the sample are provided by removing material from the sample during material removal intervals resulting in sample surfaces at the one or more depths of the sample. The depth profile data is operated upon to provide characterization of the sample at each of one or more of the plurality of depths. Such operation on the depth profile data includes obtaining measured peak areas for at least one component from the depth profile data collected at a particular depth, wherein the measured peak areas are representative of concentration contributions from a surface layer corresponding to the particular depth and also deeper layers of the sample. Calculated peak areas are determined for the at least one component corresponding to a measure of that component's concentration in the surface layer by removing concentration contributions of the deeper layers from the measured peak areas. The calculated peak areas are converted into at least concentration of the at least one component at the particular depth.

Another method for use in characterizing a sample according to the present invention comprises collecting depth profile data at a first depth of a sample by irradiating the sample of x-rays resulting in the escape of photoelectrons therefrom and detecting photoelectrons escaping from the sample. The detection of the photoelectrons escaping from the sample is provided with the use of an analyzer having an input lens receptive of photoelectrons. The input lens generally has a central axis extending therethrough. The input lens is positioned such that the central axis of the input lens is at an analyzer angle relative to the sample surface. The analyzer angle is in the range of about 45 degrees to about 90 degrees; preferably, 60 degrees to about 90 degrees, and more preferably, 90 degrees). A signal is then generated representative of the detected photoelectrons.

Upon collection of data at the first depth, material is removed from the sample exposing a second depth of the sample. The material is removed from the sample by sputtering material from a sample surface using an ion beam provided at an ion angle less than or equal to about 45 degrees relative to the sample surface (preferably, less than or equal to about 20 degrees) and including ions having ion energies of less than 500 eV.

After exposure of the second depth of the sample, depth profile data is collected at the second depth of the sample by irradiating the sample with x-rays resulting in the escape of photoelectrons therefrom and detecting photoelectrons escaping from the sample using the input lens positioned at the analyzer angle. A signal representative of the detected photoelectrons is then generated.

The depth profile data collected for at least the first and second depths may be then utilized to calculate concentration of components at the first depth. For example, such calculation may be performed according to one or more other processes summarized above.

A system for use in characterizing a sample according to the present invention is also provided. The system includes an x-ray source operable to irradiate the sample (e.g., when the sample is positioned at an analysis plane of the system) with x-rays resulting in the escape of photoelectrons therefrom. Further, the system comprises an analyzer operable to detect photoelectrons escaping from the sample. The analyzer generally includes an input lens receptive of photoelectrons, wherein the lens has a central axis extending therethrough. The input lens is positioned such that the central axis of the input lens is at an analyzer angle relative to the analysis plane that is in the range of about 45 degrees to about 90 degrees (more preferably, about 60 degrees to about 90 degrees, and more preferably, about 90 degrees). Further, the analyzer is operable to generate a signal representative of the detected photoelectrons.

Yet further, the system includes an ion source operable to provide ions for removal of material from a sample positioned at the analysis plane during material removal intervals resulting in sample surfaces at one or more depths of the sample. A computing apparatus of the system is operable to generate depth profile data based on the signals representative of the detected photoelectrons for each of a plurality of depths of the sample. The computing apparatus is further operable to use the depth profile data collected for at least a first and second depth to characterize the sample at the first depth. The second depth is at a position deeper in the sample than the first depth.

In one embodiment of the system, the ions provided by the ion source have ion energies of less than 500 eV. Further, the ion source may be operable to provide an ion beam at an ion angle less than or equal to about 45 degrees relative to the analysis plane; more preferably, the ion beam is at an ion angle less than or equal to about 20 degrees relative to the analysis plane.

In addition, the system may include an apparatus for rotating the sample during material removal intervals.

In the system above, and/or in another system for characterizing a sample, a computer apparatus may be operable to recognize depth profile data collected for each of a plurality of depths of a sample and operate on such depth profile data to provide characterization of the sample at each of one or more plurality of depths. Operation on the depth profile data may include obtaining measured peak areas for at least one component from the depth profile data collected at a particular depth, wherein the measured peak areas are representative of concentration contributions from a surface layer corresponding to the particular depth and also deeper layers of the sample. Calculated peak areas for the at least one component corresponding to a measure of that component's concentration in the surface layer may then be determined by removing concentration contributions of the deeper layers from the measured peak areas. The calculated peak areas are then converted into at least concentration of the at least one component at the particular depth.

In yet another system according to the present invention, the system comprises an x-ray source operable to irradiate the sample (e.g., when the x sample is positioned at an analysis plane of the system) with x-rays resulting in the escape of photoelectrons therefrom. The system further includes an analyzer operable to detect photoelectrons escaping from the sample. The analyzer includes an input lens receptive of photoelectrons; the input lens having a central axis extending therethrough. The input lens is positioned such that the central axis of the input lens is at an analyzer angle relative to the analysis plane. The analyzer angle is in the range of about 45 degrees to about 90 degrees (preferably, in the range of about 60 degrees to about 90 degrees, and more preferably, at an analyzer angle of about 90 degrees). The analyzer is operable to generate a signal representative of the detected photoelectrons.

Further, the system may include an ion source operable to provide ions for removal of material from the sample positioned at the analysis plane during material removal intervals resulting in sample surfaces at one or more depths of the sample. The ion source is operable to provide an ion beam at an angle less than or equal to about 45 degrees relative to the analysis plane; the ion beam including ions having ion energies of less than 500 eV.

A computing apparatus of the system is then operable to generate depth profile data based on signals representative of the detected photoelectrons for each of a plurality of depths of the sample. Further, the computing apparatus is operable to use the depth profile data collected for at least a first and second depth to characterize the sample of the first depth. The second depth is at a deeper position in the sample than the first depth.

Systems and methods according to the present invention for characterizing samples are also described herein. In particular, such systems and methods are particularly beneficial for the non-invasive analysis of thin films.

The present invention can provide an accurate measure of a component (e.g., an element and/or a chemical species) within a thin film, thickness of such a thin film, distribution or uniformity of such a component across the thin film, and/or uniformity of thickness across such a thin film, by correlating surface spectrum measurements for thin films that are obtained non-invasively with depth profile information for the thin films that is obtained invasively.

Generally, the present invention includes the collection of depth profile information for thin films of a plurality of samples formed under a set of conditions using, for example, XPS, or ESCA, depth profiling. The depth profile information is correlated with surface spectrum measurements obtained for the samples prior to removal of material in the depth profiling process so as to provide calibration information representative of such correlation. Thereafter, a characteristic of a thin film formed under the set of process conditions, e.g., dose of nitrogen in a thin nitrided silicon oxide film, can be determined based on surface spectrum measurements of the thin film and the calibration information.

A method for use in characterizing a sample according to the present invention includes providing calibration information representative of surface spectrum measurements for a plurality of samples correlated with depth profile information for the plurality of samples. Each of the plurality of samples is formed under a same set of process conditions. The depth profile information of each sample of the plurality of samples is provided using surface spectrum measurements corresponding to one or more progressively deeper depths of each sample; the one or more progressively deeper depths resulting from removal of material therefrom. Further, the method includes performing one or more surface spectrum measurements for a sample to be characterized. The sample to be characterized is also formed under the same set of process conditions. At least one characteristic of the sample to be characterized is determined based on the one or more surface spectrum measurements for the sample to be characterized and the calibration information.

In one embodiment of the method, the surface spectrum measurements for the plurality of samples are provided using a particular set of parameters. Further, the surface spectrum measurements for each of the plurality of samples are provided by irradiating the sample with x-rays resulting in the escape of photoelectrons therefrom, detecting photoelectrons escaping from the sample, and generating a signal representative of the detected photoelectrons. The surface spectrum measurements are based on the generated signals.

In another embodiment of the method, providing depth profile information for the plurality of samples is provided in a manner such as described above.

Another method according to the present invention for use in characterizing a thin film of a sample includes providing calibration information representative of surface spectrum measurements for thin films of a plurality of samples correlated with depth profile information for the thin films of the plurality of samples. Each of the plurality of samples is formed under a same set of process conditions. The calibration information is provided by providing surface spectrum measurements for the thin film of each of the plurality of samples using a particular set of parameters. Such surface spectrum measurements are provided by irradiating the sample with x-rays resulting in the escape of photoelectrons therefrom, detecting photoelectrons escaping from the sample, and generating a signal representative of the detected photoelectrons. The surface spectrum measurements are based on the generated signals. Further, providing the calibration information includes providing depth profile information in a manner as described above. With the calibration information provided, one or more surface spectrum measurements for a thin film of a sample to be characterized is performed using the particular set of parameters. The thin film to be characterized is formed under the same set of process conditions as the thin films of the plurality of samples. At least one characteristic of the thin film of the sample to be characterized is determined based on the one or more surface spectrum measurements of the sample to be characterized and the calibration information.

A system for use in characterizing a sample according to the present invention includes an x-ray source operable to irradiate a sample with x-rays when the sample is positioned at an analysis plane of the system resulting in the escape of photoelectrons therefrom, an analyzer operable to detect photoelectrons escaping from the sample (e.g., an analyzer operable to generate a signal representative of the detected photoelectrons), and an ion source operable to provide ions for removal of material from a sample positioned at the analysis plane during material removal intervals resulting in sample surfaces at one or more depths of the sample. The system further includes a computing apparatus operable to recognize calibration information representative of surface spectrum measurements for a plurality of samples (i.e., a plurality of samples each formed under a same set of process conditions) correlated with depth profile information for the plurality of samples (i.e., depth profile information provided using surface spectrum measurements performed at one or more progressively deeper depths of each of the plurality of samples, the one or more progressively deeper depths resulting from the removal of material from the sample). The computing apparatus is also operable to provide one or more surface spectrum measurements for a sample to be characterized based on a signal representative of detected photoelectrons, and thereafter, determine at least one characteristic of the sample based on the one or more surface spectrum measurements for the sample to be characterized and the calibration information.

In various embodiments of the system, the system may be configured as described in one or more of the embodiments above and/or be configured to implement one or more of the methods as described herein.

The above summary of the present invention is not intended to describe each embodiment or every implementation of the present invention. Advantages, together with a more complete understanding of the invention, will become apparent and appreciated by referring to the following detailed description and claims taken in conjunction with the accompanying drawings.

BRIEF DESCRIPTION OF THE DRAWINGS

FIGS. 5A and 5B are illustrative diagrams for use in describing analyzer angle embodiments according to the present invention.

DETAILED DESCRIPTION OF THE EMBODIMENTS

Analysis systems and depth profiling methods according to the present invention shall be described with reference to FIGS. 1-8. Such systems and methods may be used to analyze complex materials in development processes, assist to identify solutions for processing problems, identify contamination sources, improve yields in the fabrication of devices, assist in monitoring processing devices, and be used in failure analysis techniques. Further, the systems and methods may be used in the characterization of samples relating to various industrial applications, such as semiconductor devices, magnetic storage media, display technology, automotive materials, aerospace materials, polymer products, and/or biomaterials.

Further non-invasive analysis systems and methods shall be described with reference to FIGS. 9-15. Generally, such analysis systems and methods include the collection of depth profile information for thin films of a plurality of samples formed under a set of conditions using, for example, XPS, or ESCA, depth profiling. More preferably, the depth profiling is performed according to a method or system as described with reference to FIGS. 1-8. The depth profile information is correlated with surface spectrum measurements obtained non-invasively from the sample prior to removal of material in the depth profiling process to provide calibration information representative of such correlation. Thereafter, a characteristic of a thin film formed under the set of process conditions, e.g., dose of nitrogen in a thin nitrided silicon oxide film, can be determined based on surface spectrum measurements of the thin film to be characterized and the calibration information.

Figure 1:
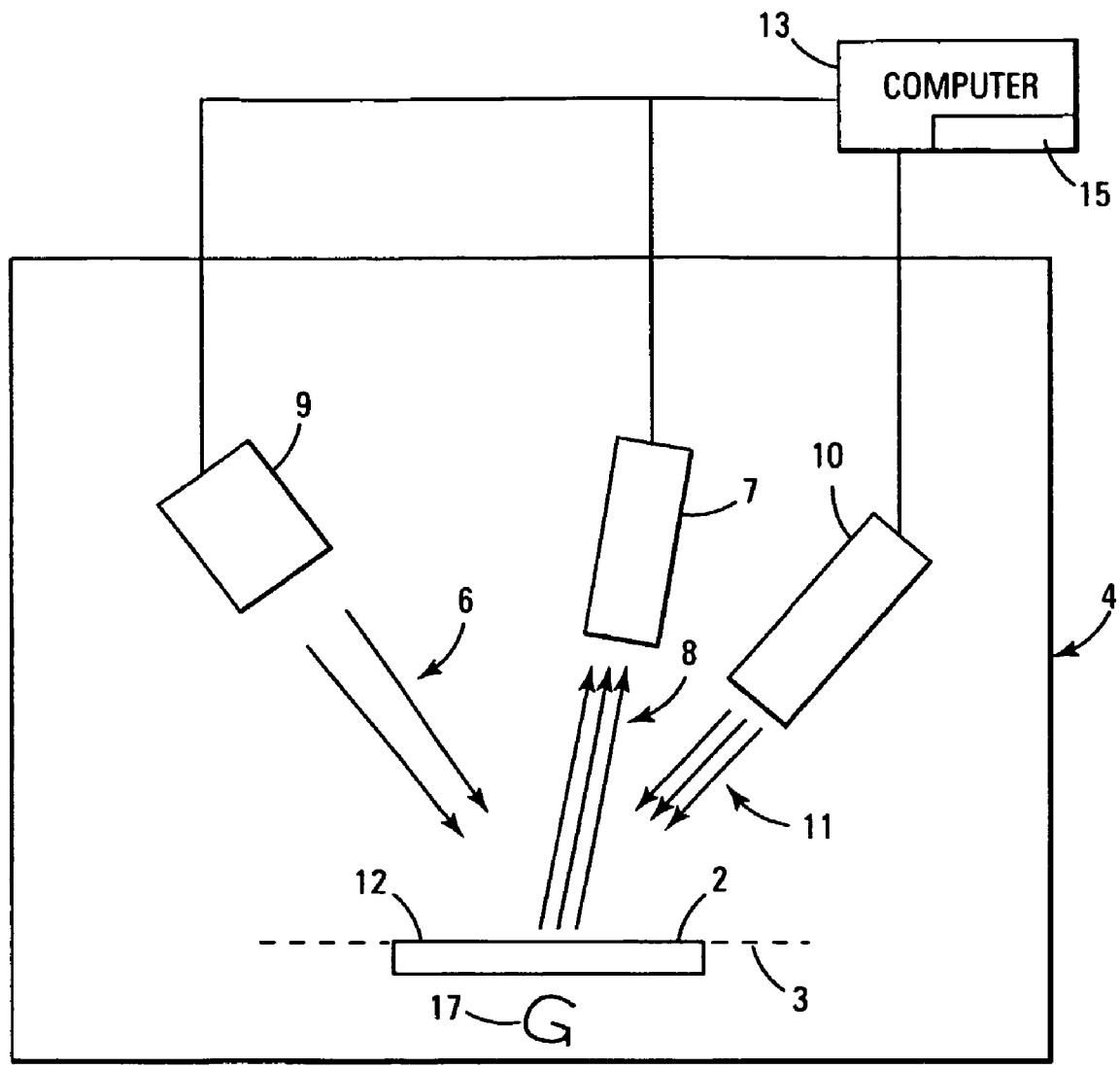
FIG. 1 is an illustrative diagram of an analysis system according to the present invention.

FIG. 1 generally shows one embodiment of an illustrative analysis system 1 operable for use in characterizing a sample 2 positioned at an analysis plane of an analysis instrument 4. Coupled to the analysis instrument 4 is a computer apparatus 13 operable under control of one or more programs 15 to carry out one or more various depth profiling and/or characterization processes, e.g., depth profiling method 120 shown generally in FIG. 3, the characterization method shown generally in FIG. 7, etc.

The sample 2 having a sample surface 12 may be formed of any one or more components. The term component is defined herein as one or more elements and/or chemical species. For example, such components may include elements and/or chemical species composing materials used in semiconductor fabrication, magnetic storage media, or any of the other various applications described above. In other words, for example, in the context of semiconductor fabrication the sample may include layers formed of oxygen, silicon, carbon, fluorine, silicon dioxide, nitrogen, etc.

Preferably, the present invention is useful in the characterization of thin films, particularly thin dielectric or insulating films. As used herein, a thin film refers to a film or layer having a thickness of less than about 10 nanometers. However, the present invention may be beneficial in characterizing films as thick as 100 nanometers and is particularly beneficial for analyzing films having a thickness of less than 2 nanometers.

Further, the present invention is particularly advantageous in characterization of certain oxide layers. For example, such oxide layers may include silicon oxide layers, oxynitride films, nitrided oxide layers, silicon oxynitride (ONO) films, etc. For example, such oxide layers may be formed as thin films having thicknesses less than about 10 nanometers, and even 2 nanometers, and used for gate oxides in the fabrication of semiconductor devices such as field effect transistors (FET). Such transistors are used in various integrated circuit devices including processing devices, memory devices, etc.

Further, the present invention is advantageous in measuring the shape and dose of thin implant regions with accurate quantitative results and chemical composition information. For example, a silicon substrate may be implanted with $BF_2$ in the formation of semiconductor devices. The present invention may be used to characterize such a formed implanted thin layer or region by depth profiling the implanted silicon substrate sample.

As one skilled in the art will recognize from the description above, the sample may take one of many different forms. For example, the sample may be a layer formed on a substrate or a region formed within a substrate, as well as any other sample formed of a material that would benefit from being characterized according to the present invention. As such, the present invention is not to be taken as limited to any particular material or structure listed herein. However, the present invention does have particular advantages in characterizing certain thin films, e.g., gate dielectric layers such as gate oxide layers.

As used herein, characterization refers to the determination of one or more characteristics of the sample being analyzed. For example, characterization may refer to the depth profiling of a sample or portion thereof, the determination of concentration of components in a sample, the distribution of such components, or the determination of one or more other physical or chemical characteristics of the sample, e.g., thickness of regions, bonding states in the regions, elemental and chemical composition in the regions. The present invention is particularly beneficial in the determination of the concentration of components (e.g., elements and/or chemical species) versus depth in the sample 2.

Preferably, computer apparatus 13 includes a computing system operable to execute software 15 to provide for the characterization of samples according to the present invention. Although the computer apparatus 13 may be implemented using software 15, executable using a processor apparatus, other specialized hardware may also be used to provide certain functionality required to provide a user with characterization of a sample. As such, the term computer apparatus 13 as described herein includes any specialized hardware in addition to processor apparatus capable of executing various software routines.

The computer apparatus 13 may be, for example, any fixed or mobile computer system, e.g., a personal computer, and/or any other specialized computing unit provided as a functional part of or as a supplement to an analysis instrument used according to the present invention. The exact configuration of the computer system is not limiting and most any device capable of providing suitable computing capabilities and/or control capabilities may be used according to the present invention. Further, various peripheral devices, such as a computer display, a mouse, a keyboard, a printer, etc., are contemplated to be used in combination with a processor in the computer apparatus 13. For example, a computer display printer may be used to display depth profile information, e.g., depth profile curves showing concentration of components (e.g., elements and/or chemical species) at depths of the sample, distributions of components across a sample at a particular depth, spectra of the components, etc.

Figure 2:
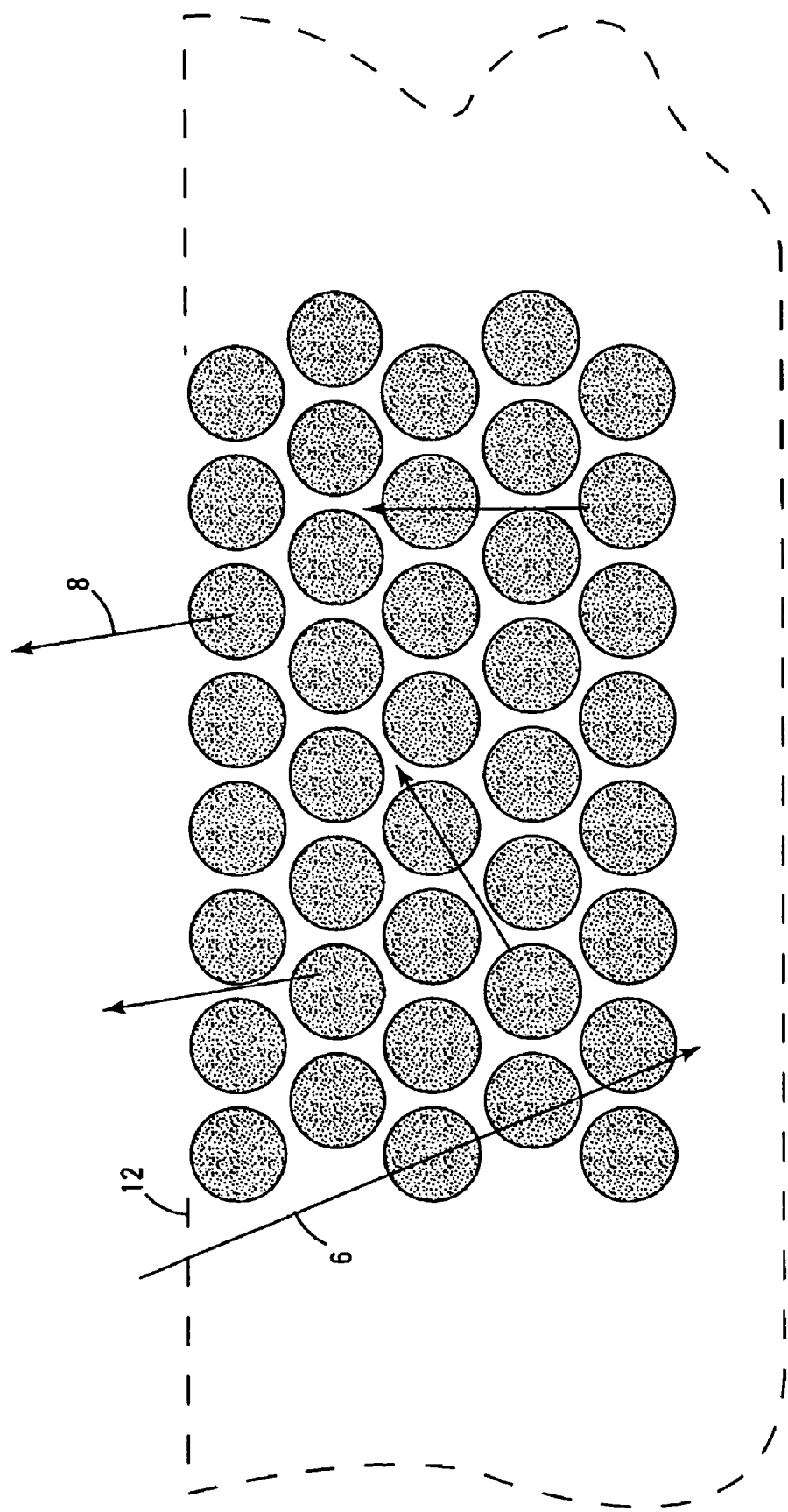
FIG. 2 is a diagram showing surface sensitivity of a sample being irradiated with x-rays for use in illustrating the present invention.

The analysis instrument 4 of the analysis system 1 according to the present invention includes an x-ray source 9 operable to irradiate the sample 2 with x-rays 6 resulting in the escape of photoelectrons therefrom. As shown in FIG. 2, the x-rays 6 penetrate deep into the sample surface 12, exciting photoelectrons 8 to escape from the sample 2. However, photoelectrons can travel only a short distance before their energy is modified due to interaction with neighboring atoms. Only photoelectrons that escape at their original energy contribute to a peak in a spectrum used for the analysis of the sample. As such, depending on the escape depth of the constituents of the sample, the average depth of analysis for a surface irradiated by x-rays 6 is in the range of about 10 Å to about 50 Å depending upon the sample material. The photoelectron energies generally include a low energy peak in the range of up to 10 eV, usually about 2 eV to 5 eV, plus higher kinetic energy peaks or lines characteristic of chemical species in the irradiated sample.

An analyzer 7 of the analysis system 1 is operable to detect photoelectrons 8 escaping from the sample. The analyzer 7 is positioned at an analyzer angle (as further described below) relative to the analysis plane 3 or, in other words, relative to the sample surface 12 which is preferably in the analysis plane. The analyzer 7 is used to detect photoelectrons for generation of a signal representative thereof to be used in the provision of depth profile data to be used for the characterization of the sample 2. Signals from the analyzer corresponding to intensity of detected photoelectrons are provided to the computer apparatus which operates on the signals to provide photoelectron energy information and thereby information on components that are present in the sample surface at the depth being analyzed.

The analysis instrument 4 further includes an ion source 10 operable to provide ions 11, e.g., an ion beam, for removal of material from the sample 2 positioned at the analysis plane 3 during material removal intervals. Such removal of material results in sample surfaces at one or more progressively deeper depths of the sample 2.

Figure 3:
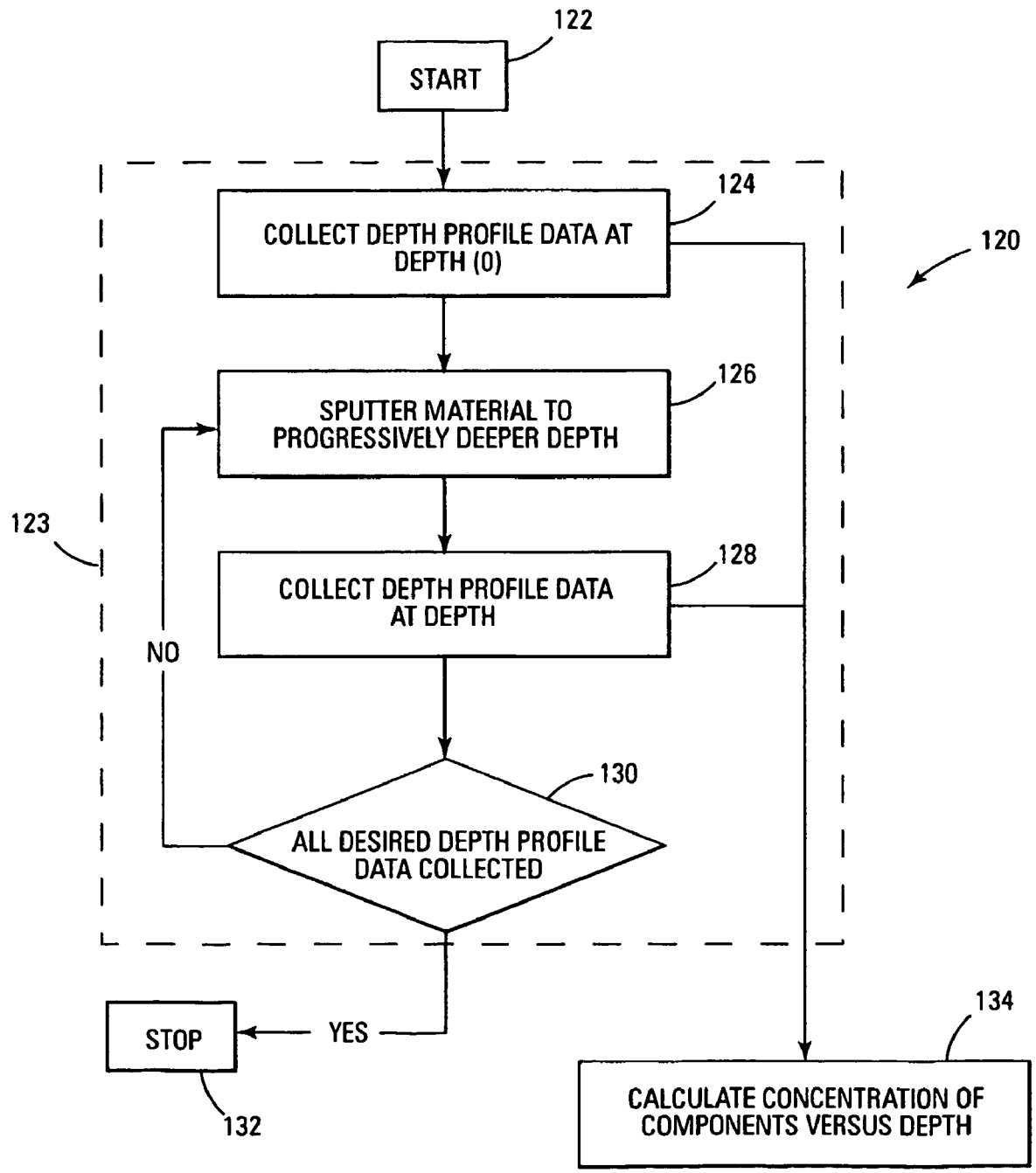
FIG. 3 is a flow diagram of a depth profiling method according to the present invention.

The analysis system 1 diagrammatically shown in FIG. 1 is operable to carry out the depth profiling method 120 as shown generally in FIG. 3. The depth profiling method 120 according to the present invention begins with an initiation of the process as indicated at block 122. Generally, the depth profiling method 120 includes collecting depth profile data, e.g., surface spectrum measurements, at each of a desired plurality of depths of the sample 2 as shown by dashed block 123.

The collected depth profile data is then provided and operated upon to calculate concentration of components (e.g., elements and/or chemical species) at the plurality of depths of the sample 2 (block 134). In the collection of the depth profile data (dashed block 123), depth profile data, e.g., surface spectrum measurements, are collected for the top layer at the surface 12 of the sample 2 (block 124). The surface 12 of the sample 2 generally corresponds to a depth(0) of the sample 2, or in other words, the initial surface being analyzed.

Thereafter, material is removed from the sample 2, e.g., material is sputtered therefrom, as shown in block 126. The removal of the surface material of the sample 2 exposes a progressively deeper material, i.e., a deeper layer, such that depth profile data may be collected at a sample surface corresponding to the progressively deeper depth, e.g., depth(l) (block 128).

As indicated by decision block 130, the depth profile cycles of removing material, e.g., sputtering material, from the sample 2 (block 126), and collecting depth profile data at progressively deeper depths (block 128) is repeated until all desired depth profile data is collected. Once the desired depth profile data is collected, the process is completed (block 132).

Upon the collection of depth profile data for at least two depths, e.g., depth(0) and depth(1), calculation of concentration of components (e.g., elements and/or chemical species) may be calculated as further described below with reference to illustrative embodiments shown in FIGS. 7 and 8. Generally, the calculation of concentration of components at each particular depth (block 134), e.g., depth(0), is performed based on the depth profile data collected at such particular depth, e.g., depth(0) and depth profile data collected at a subsequent deeper depth, e.g., depth(1).

In the characterization of certain films, particularly thin films or layers, conventional XPS techniques have been used to calculate a depth profile. However, information from many layers over a distance corresponding to the photoelectron escape depth is mixed together, resulting in a smearing out of the depth profile and limiting depth resolution. Such depth resolution can be enhanced with the use of a lower analyzer take off angle detecting photoelectrons escaping from the surface at a low take-off angle (e.g., much less than 40 degrees relative to the sample surface, preferably about 10 degrees to 20 degrees). However, as described further below, such a lower analyzer angle may restrict the size of samples which can be characterized, result in lower sensitivity, and have slower capture of profile data, e.g., low analyzer angles require more time, relative to higher analyzer angles, to capture sufficient signal for generation of depth profile data used in the characterization of the sample.

Further, in conventional XPS depth profiling, in particular with respect to depth profiling of thin films, such thin films are difficult to sputter. For example, removal of extremely small portions of a thin film or layer, e.g., 1 or 2 Å, is difficult and most conventional sputter processes may create chemical damage to the thin film and/or induce alteration of the distribution of components within the film.

To improve the characterization of such thin films, analysis system I (e.g., an XPS or ESCA system) is configured with one or more particular features and/or is operated under one or more particular parameters so as to eliminate problems associated with the conventional methods. Such configurations and/or parameters are described further below with reference to one or more embodiments shown in the illustrative figures. One skilled in the art will recognize that one or more of such parameters and/or features of the analysis system 1 as further described below may be used in combination with other features or may be used alone to enhance the characterization of the sample 2 according to the present invention.

The present invention may be employed by modifying an analysis system distributed under the trade designations PHI Quantum 2000 Scanning ESCA Microprobe™ and PHI Quantera Scanning XPS Microprobe™ available from Physical Electronics, Inc. (Eden Prairie, Minn.). The systems may be modified and/or operated at one or more of the parameters described herein to provide for thin film analysis.

Figure 4:
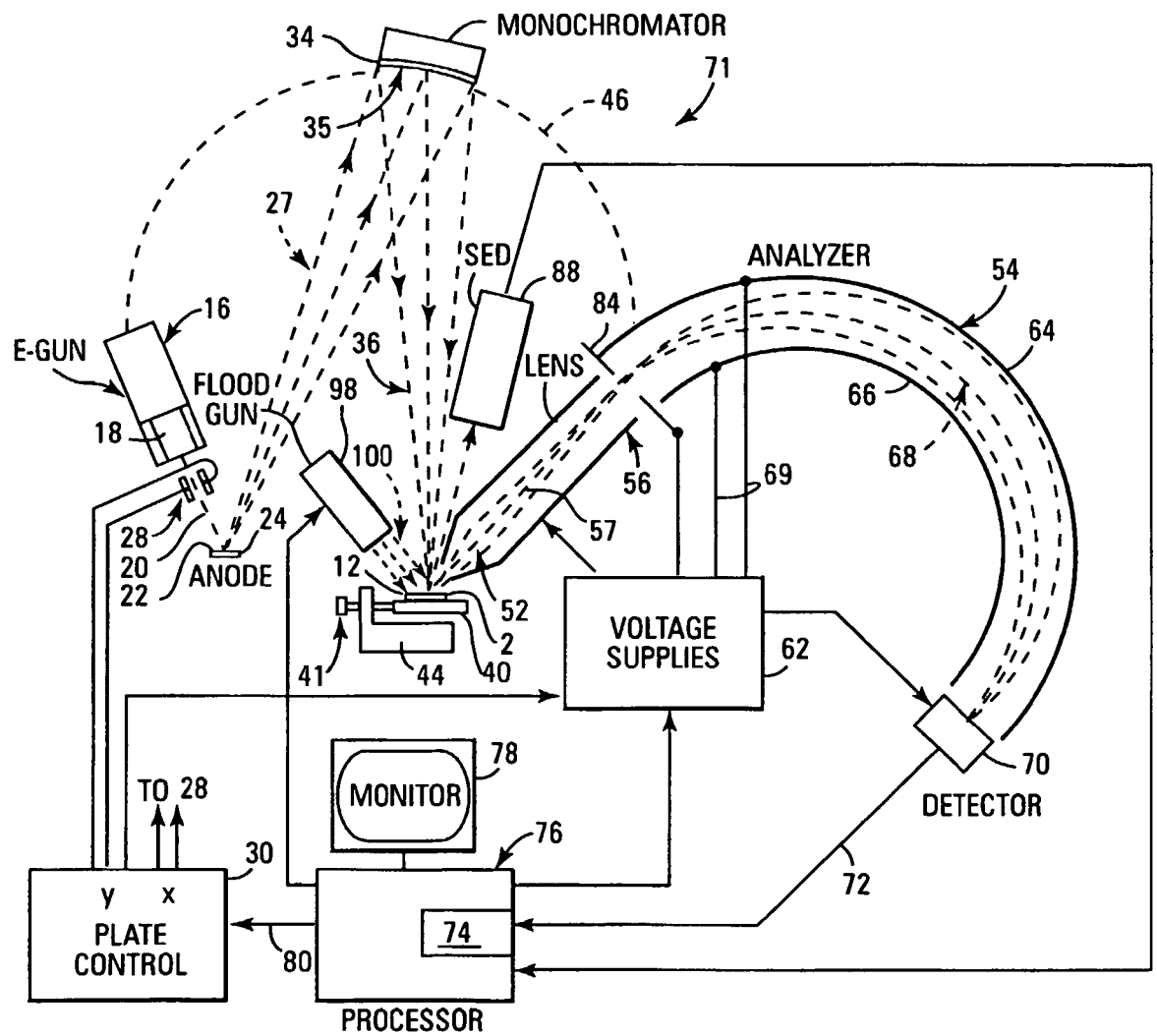
FIG. 4 is a schematic diagram of one illustrative embodiment of a portion of the system shown in FIG. 1.

FIG. 4 shows in more detail one illustrative embodiment of portions of an analysis system I operable for carrying out the characterization according to the present invention. The analysis instrument 71 shown in FIG. 4 for analysis of a sample 2 provides a more detailed illustrative embodiment of the x-ray source 9, the analyzer 7, and the computer apparatus 13 shown generally in FIG. 1. FIG. 4 was previously described in U.S. Pat. No. 5,315,113 to Larson et al., issued 24 May 1994, and entitled "Scanning and High Resolution X-ray Photoelectron Spectroscopy and Imaging." The detailed diagram of FIG. 4 is but one illustrative embodiment of an x-ray source and an analyzer that may be used according to the present invention and is not to be construed as limiting the present invention to any particular components shown therein.

The instrument 71 of FIG. 4 includes an electron gun 16 having an appropriate electron lens system 18 for focusing the electron beam 20 onto the surface 22 of a target anode 24. The electron gun 16 may be a conventional type, modified to optimize for higher power and larger beam size. The gun beam 20 is focused to a selected spot on the anode surface 22. The spot is preferably as small as practical, e.g., down to about 4 microns. The focusing of the beam 20 onto the spot of the anode surface results in the generation of x-rays 27 from the anode 24 and, in particular, from the selected anode spot. The electron gun may be any suitable gun such as one operable at 20 kV over 1 watt to 60 watts with a selectable beam size of 4 microns to 50 microns, as described in U.S. Pat. No. 5,315,113.

The target anode 24 may be formed of any metal such as aluminum that provides a desired x-ray emission energy band. For example, the band is generally substantially a line of small energy width. Preferably, the target anode is at or near ground potential, and the gun cathode is operated at a negative voltage, for example, −20 kV, with respect to the anode to effect generation of x-rays including the desired band of x-rays of predetermined energy. In one preferred embodiment, the selected energy band is the aluminum K-alpha line at 1.4866 keV.

Deflection plates 28 selectively direct or aim the electron beam 20 from the electron gun 16 to the spot on the anode 24 which is selected out of an array of such spots on the anode surface 22. Voltages from a deflection plate control 30, controlled by a processor 76 via line 80, are applied to the deflector plates, which are arranged in both x and y axes, to establish the amount of deflection of the beam, and thereby the selected position of the spot. The spot may be held stationary. Alternatively, the control 30 may provide rastering of the focused electron beam 20 across the flat surface of the anode, e.g., over the array of anode spots across the anode surface, and the x-rays 27 are emitted sequentially from successive anode spots. For example, raster speed may be 100 Hz in the dispersive direction and 10 kHz in the non-dispersive direction.

A Bragg crystal monochromator 34, advantageously single-crystal quartz, is disposed to receive a portion of the x-rays 27 from the anode 24. The monochromator has a crystallographic orientation and a concave configuration 35 to select and focus a beam of x-rays 36 in the desired energy band, e.g., the K-alpha line, as an x-ray spot on the sample surface 12 to be analyzed. The x-ray spot is an image of the anode spot on the sample surface 12. Alternatively, rastering of the x-ray spot may be used to cover a desired area of the sample surface. The sample 2 rests on a stage 40 advantageously having orthogonal micrometer positioners 41 for manual or motorized positioning with respect to a support 44 in the instrument. The sample 2 may be moved to provide coverage over an even larger surface area.

Although a Bragg crystal monochromator is preferred, other focusing apparatus may be suitable. Such focusing apparatus may include grazing incidence mirrors, Fresnel zone plates, and synthetic multilayer devices of alternating high and low density material (e.g., tungsten and carbon). In each case, the reflector is curved to focus the diffracted x-rays onto the specimen.

A suitable arrangement of components for the analysis instrument 71 is based on the conventional Rowland circle 46. In this arrangement, the anode surface 22, the crystal 34, and the sample surface 12 are substantially on the circle, for example, as taught in U.S. Pat. No. 3,772,522, to Hammond et al., issued 13 Nov. 1973 and entitled "Crystal Monochromator and Method of Fabricating a Diffraction Crystal Employed Therein."

The x-rays 36 cause photoelectrons 52 to be emitted from the selected active pixel area of the sample. The electron energies generally include a low energy peak in the range of up to 10 eV, usually about 2 to 5 eV, plus higher kinetic energy peaks or lines characteristic of chemical species (e.g., chemical elements and/or their electron bondings) in the selected pixel area. In the case of rastering, the characteristic photoelectrons vary with any varying chemistry across the array of pixel areas, and the low energy electrons (commonly known as "secondary electrons") vary with topography, as well. Detection and/or analysis of the photoelectrons is used to provide information regarding the sample surface at a selected pixel area or across the rastered array of areas of the sample surface. There also may be Auger electrons which, for the present purpose, are included in the term "photoelectrons" as they are caused by the x-rays.

In one embodiment of the invention, an electron energy analyzer 54 receives a portion of the photoelectrons 52. The analyzer may be a known or desired type, generally either magnetic or electrostatic, which deflects the photoelectrons in a predetermined path 68 according to electron energy and then to a detector 70. A selected control, generally an electrical signal (current or voltage), is applied to the deflector to establish the amount of deflection and so is representative of selected energy of photoelectrons deflected in the predetermined path. In a magnetic analyzer such as a magnetic prism, a current signal through the magnet coils is appropriately selected, and in an electrostatic analyzer a deflecting voltage signal is selected.

One useful type of electrostatic energy analyzer is a cylindrical type described in U.S. Pat. No. 4,048,498, to Gerlach et al., issued 13 Sep. 1977 and entitled "Scanning Auger Microprobe with Variable Axial Aperture." In a preferable alternative, as shown in FIG. 4, the analyzer 54 is a hemispherical type as described in U.S. Pat. No. 3,766,381, to Watson, issued 16 Oct. 1973 and entitled "Apparatus and Method of Charge-Particle Spectroscopy for Chemical Analysis of a Sample." The analyzer also includes a lens system 56 such as an electrostatic lens for the input to the analyzer. The lens system 56 has a central axis 57 therethrough along which system 56 lies. The lens system 56 may combine objective and retarding functions to collect photoelectrons emitted from the effective pixel area and direct them into the analyzer in the desired kinetic energy range.

The electrostatic lens system 56 may be conventional, for example, a PHI Omnifocus IV™ lens available from Physical Electronics Inc. The lens should include pairs of orthogonal deflection plates with applied voltages from a source 62. The voltages are selected, varied, or oscillated via the processor 76 in cooperative synchronization with positioning or rastering of the primary electron beam 20, under control of the processor, to centralize off-axis photoelectrons so that a substantial portion of the electrons reach the slit 84 and enter into the analyzer 54.

An alternative for the objective lens function is a magnetic lens, advantageously of a type variously known as an immersion lens, a single pole piece lens or a snorkel lens as described in U.S. Pat. No. 4,810,880, to Gerlach, issued 7 Mar. 1989 and entitled "Direct Imaging Monochromatic Electron Microscope." This objective lens is situated below the sample so that the magnetic field of the lens collects a substantial portion of the emitted photoelectrons from the sample surface. To achieve this, the sample is placed proximate the immersion lens, the sample being interposed between the immersion lens and a separate electrostatic lens which form the lens system. More generally, the sample is located between the immersion lens and the analyzer. The magnetic lens may have a collection zone of electrons emitting from a portion of specimen surface being rastered.

Yet further, preferably, the lens system is an electrostatic lens with two spherical grids, similar to the Omega™ lens available from Physical Electronics Inc. Such a lens system is used in the PHI Quantum 2000 Scanning ESCA Microprobe™ available from Physical Electronics Inc.

Returning to FIG. 4, with a selected voltage from a voltage source 62 applied via lines 69 across the hemispheres 64, 66 of the analyzer, electrons of selected energy travel in a narrow range of trajectories 68 so as to exit the analyzer into the detector 70. The latter may be a conventional multichannel detector, for example, having 16 channels for detecting a small range of electron energies passed by the analyzer in slightly different trajectories. A further lens (not shown) may be placed between the analyzer and the detector, if desired or required for certain types of detectors.

Signals from the detector 70 corresponding to intensity of photoelectron input are carried on a line or lines 72 (via an appropriate amplifier, not shown) to an analyzing portion 74 of the processing unit 76 which combines control electronics and computer processing. The processing provides electron energy information and thereby information on components that are present and emitting the photoelectrons from the particular sample surface area.

The information is stored, displayed on a monitor 78, and/or printed out in the form of images, numbers, and/or graphs. By cooperating the display (which herein includes the processing) with the electron beam directing means 28, 30, via line 80 from the processor to the controller 30, a mapping of the components in the selected or scanned surface area is effected and displayed. The mapping provides sample surface information corresponding to the selected pixel area location, or the rastered array of pixel areas on the sample surface.

Other portions of the instrument 71, such as the secondary electron detector 88 and electron gun 98 providing ions 100, are used as described in U.S. Pat. No. 5,315,113.

According to the present invention, and advantageously used in the characterization of thin films, the lens system 56 is positioned at an analyzer angle for improved and faster data collection. The lens system 56 generally extends along a central axis 57 from a photoelectron receiving end 59 to an end coupled to hemispherical portions of the analyzer 54.

Preferably, according to the present invention as illustrated in FIG. 5A, the lens system 56 is positioned at an analyzer angle θ that is in the range of about 45 degrees to 90 degrees relative to the analysis plane of the instrument, corresponding to the sample surface being analyzed. The analyzer angle θ is represented by the angle between the analysis plane and the central axis 57 along which the lens system 56 lies. More preferably, the lens system 56 is positioned at an analyzer angle in the range of 60 degrees to 90 degrees; and even more preferably, the analyzer angle is about 90 degrees.

With the lens system 56 of the analyzer 54 positioned in such a manner, detection of a greater number of escaping photoelectrons from the sample 2 upon irradiation by x-rays 36 is accomplished and a signal adequate for use in depth profiling can be acquired in a considerably reduced amount of time relative to capture of such a signal when the lens system 56 is positioned at a low analyzer angle, e.g., less than 20 degrees, as generally represented in FIG. 5B. With use of such a high analyzer angle, component sensitivity in characterization of the sample is improved. Further, detection limits for trace elements have also been shown to be better with use of a high analyzer angle relative to processes using a low analyzer angle.

Further, as shown in FIG. 5B, positioning of the lens system 56 at a low analyzer angle restricts the placement of the lens system relative to the sample. For example, a lens system is generally of a size such that at low analyzer angles, the lens system 56 must be positioned only near the edge of the sample 2. As such, use of a low analyzer angle may restrict the size of sample 2 that can be characterized. For example, positions of the sample surface away from the lens system 56 shown in FIG. 5B at the end 61 of the sample 2 are not easily characterized or effectively characterized with the lens system 56 positioned near the opposite edge of the sample 2. With a high analyzer angle, any position on a large sample, such as semiconductor wafers and hard disk media, can be analyzed as the sample itself does not restrict where the lens system 56 can be placed.

With the lens system 56 positioned at a high analyzer angle (e.g., about 45 degrees to about 90 degrees), photoelectrons having corresponding photoelectron take-off angles relative to the sample surface can be received by the lens system 56. For example, with the lens system positioned at 90 degrees, photoelectrons having a photoelectron take-off angle that falls in a cone of +/−20 degrees that is centered at 90 degrees can be detected using the analyzer. Likewise, if the analyzer is positioned at 60 degrees, photoelectrons escaping from the sample 2 at a photoelectron take-off angle that falls in a cone of +/−20 degrees that is centered at 60 degrees will be captured by the analyzer 54.

It will be recognized that use of the high analyzer angle θ, e.g., in the range of about 45 degrees to about 90 degrees, relative to the analysis plane, results in an analysis depth(d) as shown in FIG. 5A that is much deeper than the analysis depth(d) shown in FIG. 5B when a low analyzer angle is utilized. As such, the signal generated based upon the detected photoelectrons results in depth profile data at a particular depth that includes contributions from depths that are deeper in the sample. In other words, the measured depth profile data using the high analyzer angle results in signal containing contributions from the sample 2 that are deeper within the sample 2 than the thickness which is desirably analyzed at depth(d0). However, with use of a differential profile depth correction algorithm, as further described below with reference to FIGS. 7 and 8, the depth profile data collected using the high analyzer angle can be corrected using depth profile data collected subsequently, e.g., collected for a deeper depth(d1).

The ion source 10 shown in FIG. 1 for removal of surface material from the sample 2 is also configured and operated at advantageous parameters for use in the characterization of thin films. The ion source 10 may be any suitable ion gun. For example, in one suitable ion gun, an ionization chamber encloses a thermionic filament emitting electrons that are accelerated by the positive potential of a tubular grid to ionize argon gas therein. In tandem, after an opening in the ionization chamber are a cylindrical condenser lens, an aperture, a pair of beam bending plates, a cylindrical objective lens, and, optionally for steering, a cylindrical set of quadruple or octuple deflection plates. A tube containing these elements is set at a relatively low float voltage. The ions may be accelerated through the tube from the high voltage grid and slowed down to the desired energy and passed into a grounded conical exit ring and thence to ground and sample 2. Although the foregoing illustrates a suitable exemplary embodiment of a source of ions, any conventional or desired source of low energy ions that can be adapted for the analysis instrument according to the present invention may be used. For example, such an ion gun is described in U.S. Pat. No. 5,990,476, issued 23 Nov. 1999 to Larson et al., and entitled "Control of Surface Potential of Insulating Specimens in Surface Analysis."

Further, the PHI Quantum 2000 Scanning ESCA Microprobe™ and PHI Quantera Scanning XPS Microprobe™ available from Physical Electronics, Inc. (Eden Prairie, Minn.) previously cited herein provide an ion beam for use in depth profiling, e.g., depth profiling being generated by alternately collecting depth profile data and removing material via ion beam sputtering. The ion beam may remove material at a stationary spot or can be rastered to remove a larger surface area to be further analyzed.

Figure 6:
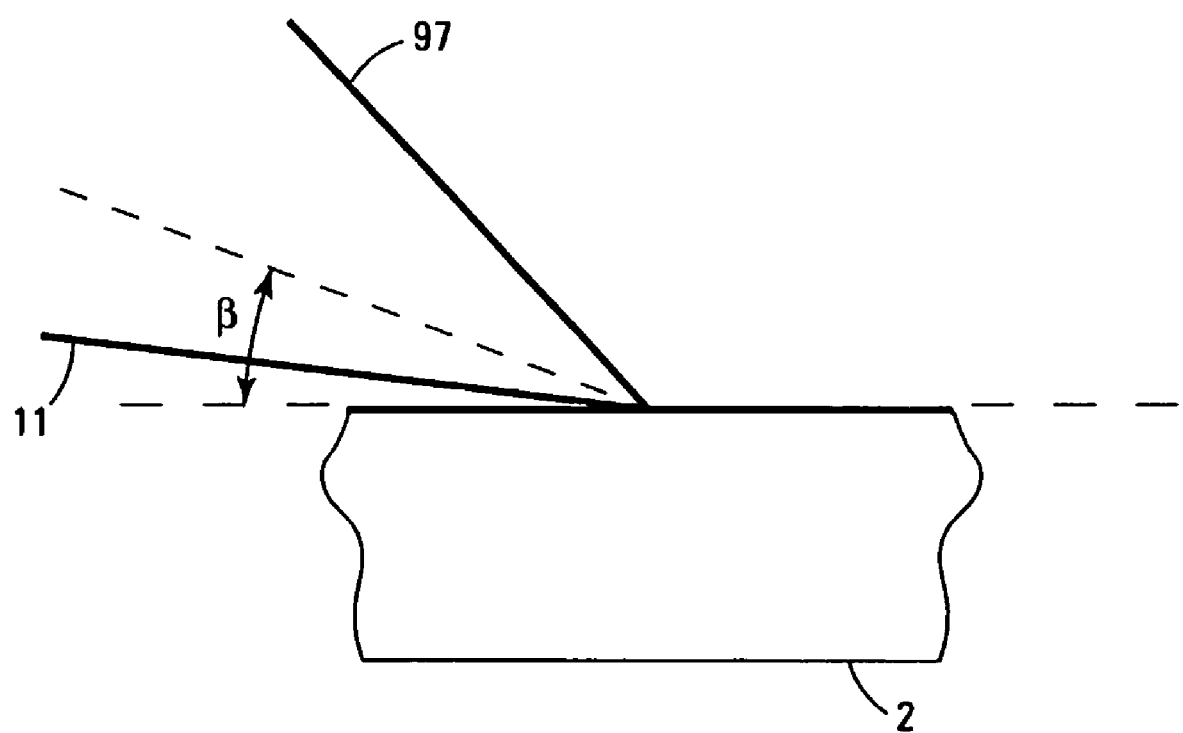
FIG. 6 is an illustrative diagram for use in describing removal of material from a sample surface according to the present invention.

According to the present invention, removal of material for the sample 2 using the ion source 10 is preferably accomplished with an ion beam at a low ion angle. FIG. 6 illustratively shows an ion beam 11 falling within a preferred range of low ion angle $\beta$ for the ion beam of less than about 45 degrees relative to the sample surface, and also a beam 97 falling outside the range. Preferably, the low ion angle $\beta$ is about 20 degrees.

In addition to the use of a low ion angle for removing material to progressively obtain deeper depths of the sample such that depth profile data may be collected at such depths, the ion beam preferably comprises ions of low ion energy. Preferably, such ion energy is less than 500 eV.

With use of such low energy ions and low ion angles, chemical damage to the thin film is minimized and also ion induced alteration of the distribution of components within the thin film is reduced.

In addition, the quality of the sputtering process may be improved through the use of Zalar™ rotation. In Zalar™ rotation, the sample is rotated during the sputter process. Such rotation of the sample during sputtering minimizes surface roughness and reduces cone formation. Further, interface resolution is maintained throughout the depth of the entire thin film structure. Rotation of the sample 2 is generally represented by circular arrow 17, as shown in FIG. 1. For example, a computer-driven stage of the analysis instrument 4 may be rotated about a selected analysis point.

In addition, to further enhance depth resolution, ions heavier than argon ions may be used for the sputtering process. For example, xenon ions may be used instead of argon ions.

As briefly described above, by sequentially sputtering and collecting depth profile data at a plurality of depths using the analyzer at a high analyzer angle, a differential profile depth correction algorithm can be applied to the collected depth profile data to provide high sensitivity and high depth resolution in providing a compositional depth profile for the sample 2. The characterization method 200 for implementing the correction algorithm and calculating the concentration of components (e.g., elements and/or chemical species) versus depth is shown generally in FIG. 7.

In the characterization method 200, the depth profile data collected at a plurality of depths is recognized and operated upon to calculate concentration of components in the sample (block 201). The concentration of components at each of the desired depths is determined by generally removing a portion of data collected at the depth for which component concentration is to be determined based on depth profile data collected at one or more subsequent depths (block 202). Preferably, the data removed is based on depth profile data collected for the depth immediately following the depth for which concentration is to be determined. In other words, depth profile data collected at depth(1) is used to determine the concentration of components at depth(0). Likewise, depth profile data collected at depth(2) is used to determine the concentration of components at depth(1).

As described previously, measured depth profile data collected at a high analyzer angle generally includes contributions from depths deeper than desired, particularly with respect to characterizing thin films. In other words, for example, depth profile data collected at depth(0) includes concentration contributions not only from depth(0), but also concentration contributions from depths deeper than depth (0), e.g., concentration contributions from depth(1), depth(2), etc. By removing the deeper depth concentration contributions from the depth(0) depth profile data, an accurate calculated concentration of components at depth(0) can be determined.

After the deeper depth contributions are removed from the depth for which concentration is to be determined, the calculated depth profile data (i.e., measured depth profile data with the deeper depths removed) can be converted to concentration of components at the depth (block 203). As provided by decision block 205, the calculations are continued for each depth at which a concentration of components is to be calculated. Once all concentrations for desired depths are calculated, the process is completed (block 207).

Figure 7:
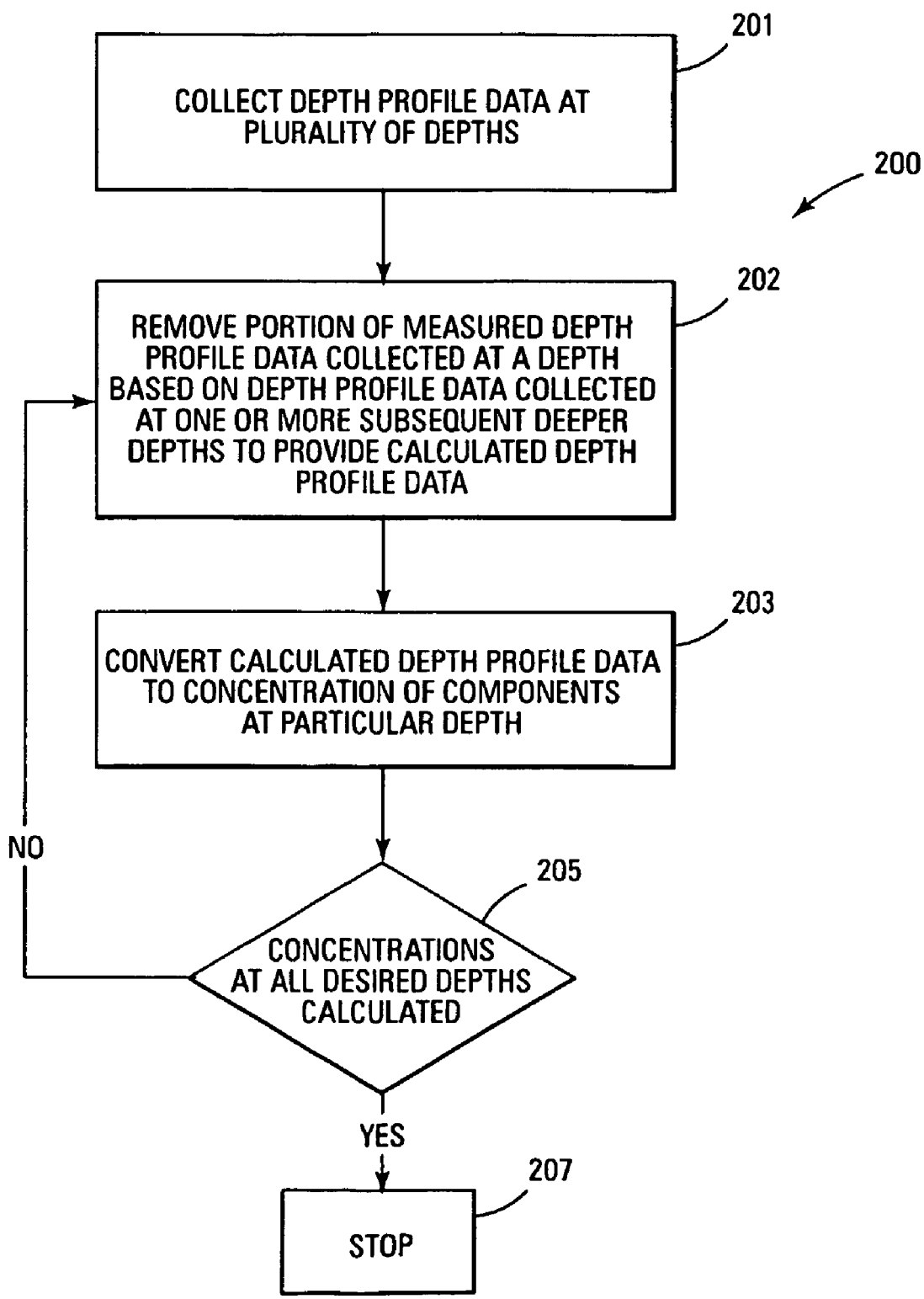
FIG. 7 is a generalized flow diagram of a characterization method, e.g., a calculation method, for determining concentration of components (e.g., elements and/or chemical species) versus depth according to the present invention as shown generally in FIG. 3.
Figure 8:
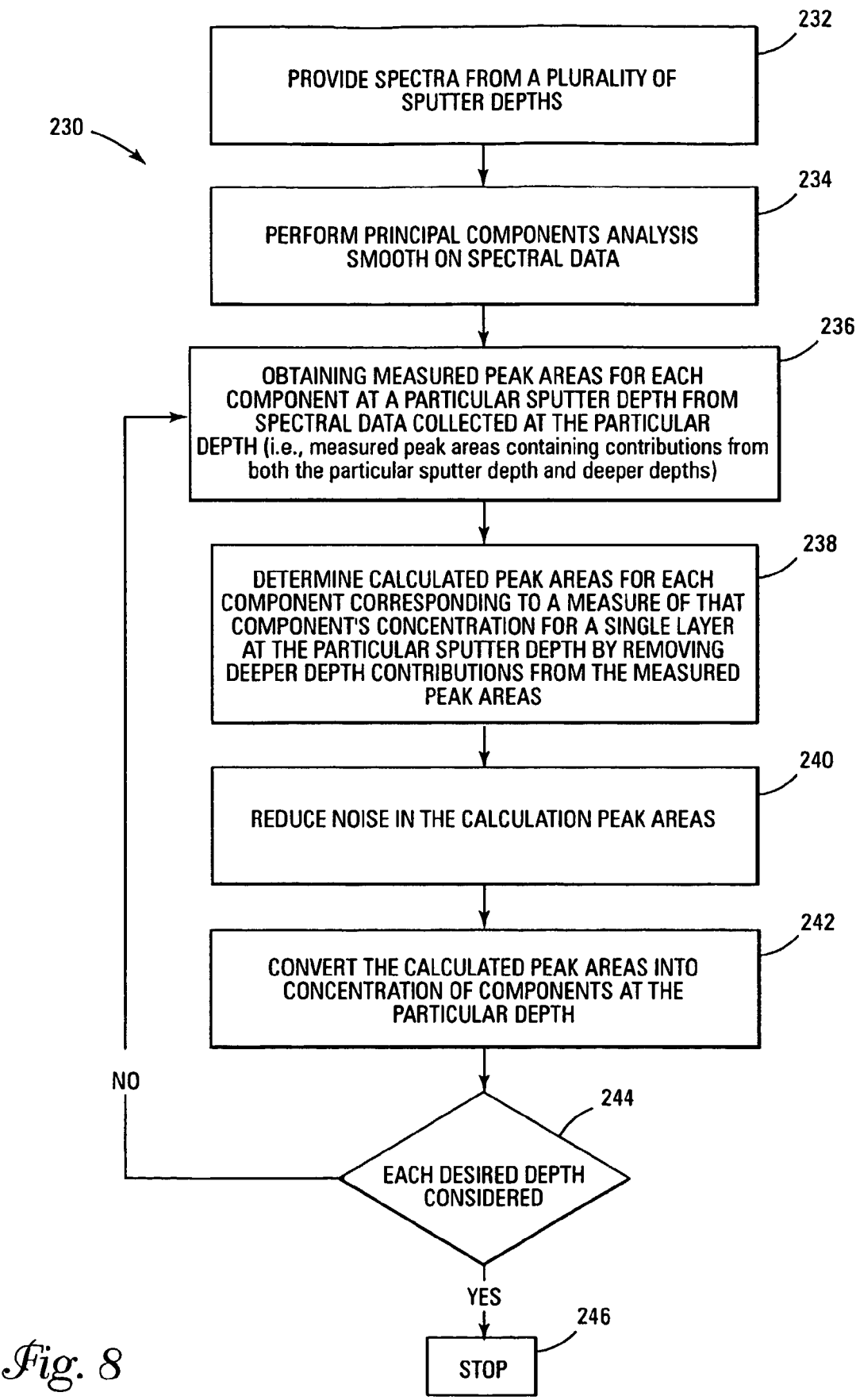
FIG. 8 is a more detailed flow diagram of one illustrative embodiment of the characterization method shown in FIG. 7.

FIG. 8 shows a flow diagram of a characterization method 230 which is a more detailed exemplary embodiment of a method generalized in the flow diagram shown in FIG. 7. The raw depth profile data collected at each sputter depth and provided to be operated upon by the correction algorithm according to the present invention generally includes spectra, i.e., electron counts versus energy, over small energy intervals containing the characteristic photoelectron peak for a particular component. There is one spectrum for each component at each sputter depth. For example, for a typical gate oxide layer, there may be silicon, oxygen, and nitrogen spectra at each sputter depth.

With such spectra provided from surface spectrum measurements at a plurality of sputter depths (block 232), principal components analysis (PCA) can be performed to smooth the data (block 234). As is generally known, principal components analysis is a technique which involves an eigen analysis of the covariance matrix. Principal components analysis is generally well known as a process for using the information in the entire data set to remove noise in each spectrum. Principal components analysis is preferably applied to the spectra from a plurality of depths, however, it is optional according to the present invention.

To attain the concentration of components at a particular depth, the following process is used for each depth at which concentration is to be determined. Such repetition for each depth is acknowledged by the decision block 244. As shown at block 244, after concentration has been determined at a particular depth, the process is repeated for a progressively deeper depth until all desired depths have been considered. Thereafter, the process is stopped (block 246).

To determine the concentration of components at a particular depth, first, measured peak areas are obtained for each component at each of a plurality of sputter depths. Such measured peak areas are obtained from the spectral data by subtracting the background and integrating the peak or by a least squares fitting of the spectral data with standard peak and background shapes. Such techniques are generally known to one skilled in the art.

Since the data has been preferably collected at a high analyzer angle, the measured peak areas contain contributions from the top layer and deeper layers. The portion of the measured peak area attributable to a single sputter layer (i.e., the calculated peak area) may be calculated by subtracting that fraction of the measured peak area arising from the deeper layers (block 238). "$A_n$" is the measured peak areas for one component at the nth sputter interval (block 236) containing contributions from deeper layers. "$A_{n'}$" is the calculated peak areas corresponding to the contribution from a single layer. If "f" is the fraction of the signal arising from the deeper layers, then $A_{n'}$, corresponding to the contributions of a single layer is calculated from: $A_{n'} = (A_n - f A_{n+1})/(1-f)$). This calculation is performed for each component of the film.

In many cases, it may be sufficiently accurate to use one value of f for all components, but, in general, it is known that f depends upon kinetic energy. Therefore, it is more accurate to use a separate value for each component. As is known to one skilled in the art, computer programs are available which can provide the energy dependence for the inelastic mean free path, and therefore f.

A plot of $A_{n'}$ (area versus depth) is inevitably noisier than a plot of the raw peak areas, $A_n$. This noise may be reduced (block 240) by various known smoothing methods such as a binomial smooth or a Savitzky-Golay smooth. Such smoothing is optional, but is preferred to attain a more realistic characterization of the sample.

The calculated peak areas, $A_{n'}$, can then be converted into concentrations of components at each sputter depth (block 242) using known techniques. For example, at each sputter depth, the calculated peak areas can be divided by component sensitivity factors and normalized so that the concentration of all components sums to 100%.

Further, to generate a depth profile, if the sputter rate is known, sputter time can be converted to depth, as would be known to one skilled in the art. With the concentration of components converted for each particular depth (block 242), such information may be plotted, displayed, or otherwise relayed to a user.

Figure 9:
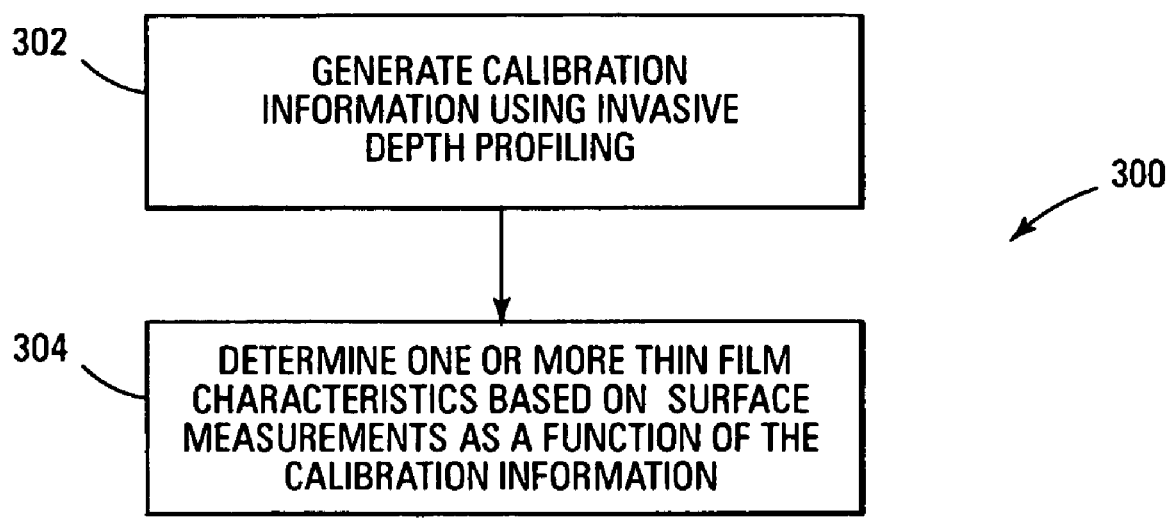
FIG. 9 is a general flow diagram of a non-invasive characterization method according to the present invention.

FIG. 9 shows a general flow diagram of a non-invasive characterization method 300 according to the present invention which uses invasive depth profiling, such as depth profiling using the methods and systems described above, to generate calibration information (block 302) The calibration information can then be used in conjunction with surface spectrum measurements of a sample to non-invasively determine one or more characteristics of the sample (block 304).

Figure 10:
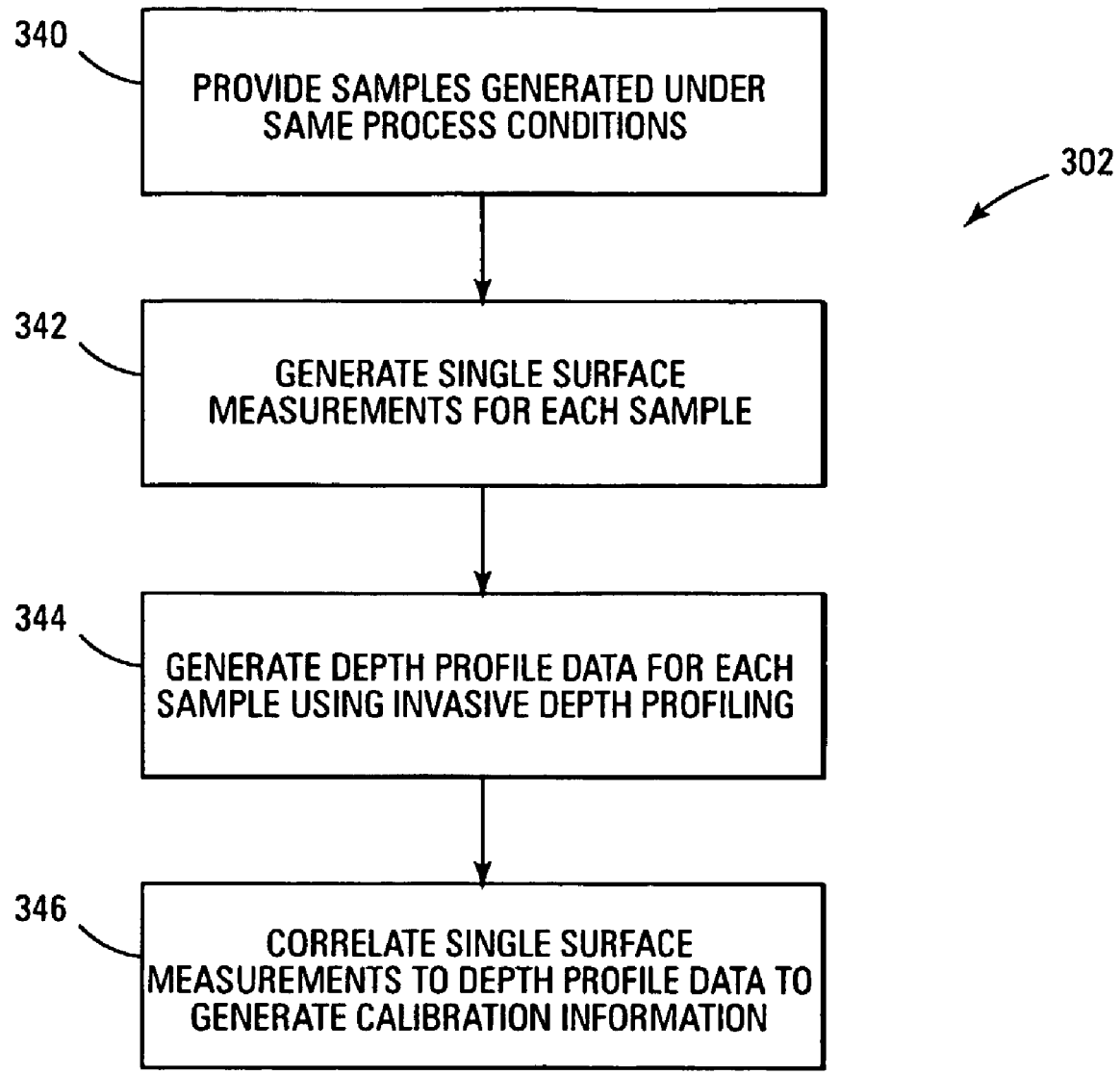
FIG. 10 is a more detailed flow diagram of one illustrative embodiment of a method for generating calibration information according to the present invention which is generally shown in FIG. 9.

More specifically, the process of generating calibration information (block 302) is shown in further detail in the flow diagram of FIG. 10. FIG. 10 shows a flow diagram of one illustrative embodiment of a method for generating calibration information.

To generate the calibration information, a plurality of samples, e.g., thin films formed on a substrate, are provided (block 340). Each of the plurality of samples are formed under the same process conditions. For example, the samples may each include a thin nitrided silicon oxide layer as further described below, or any other thin film for which characterization is desired. Further, as previously described herein, the sample may take one of many different forms. However, the present invention is particularly advantageous in characterizing thin films.

Surface spectrum measurements are collected for each sample (block 342). Such surface spectrum measurements are non-invasive measurements generated non-invasively before removal of material from the sample, e.g., at the beginning of depth profiling or before depth profiling is performed. For example, an x-ray source irradiates the sample with x-rays resulting in the escape of photoelectrons therefrom. The x-rays penetrate deep into the sample surface, exciting photoelectrons to escape from the sample. However, photoelectrons can travel only a short distance before their energy is modified due to interaction with neighboring atoms. Only photoelectrons that escape at their original energy contribute to a peak in surface spectrum measurement used for the analysis of the sample.

In other words, the average depth of analysis for a surface irradiated by x-rays depends on the escape depth of the constituents of the sample and, therefore, the detected photoelectrons are representative of only a certain depth of the sample. As such, the signal generated based on the detected photoelectrons is not necessarily representative of the entire desired depth to be analyzed. In other words, for example, the surface measurement would not be representative of the concentration of a component that extends into such deeper depths.

However, if depth profile data is generated for each sample of a plurality of samples using invasive depth profiling techniques (block 344), the single surface spectrum measurements for such samples can be correlated to the depth profile data to generate calibration information (block 346). As used herein, calibration information refers to any relational information between non-invasive surface spectrum measurements of a sample and information characterizing or for use in characterizing a sample, e.g., thin film. For example, such calibration information may take the form of concentration information over a depth of the sample as it relates to non-invasive surface spectrum measurements, thickness information as it relates to non-invasive surface spectrum measurements, concentration error information as it relates to non-invasive surface spectrum measurements, uniformity of thickness information as it relates to non-invasive surface spectrum measurements, etc.

Figure 12:
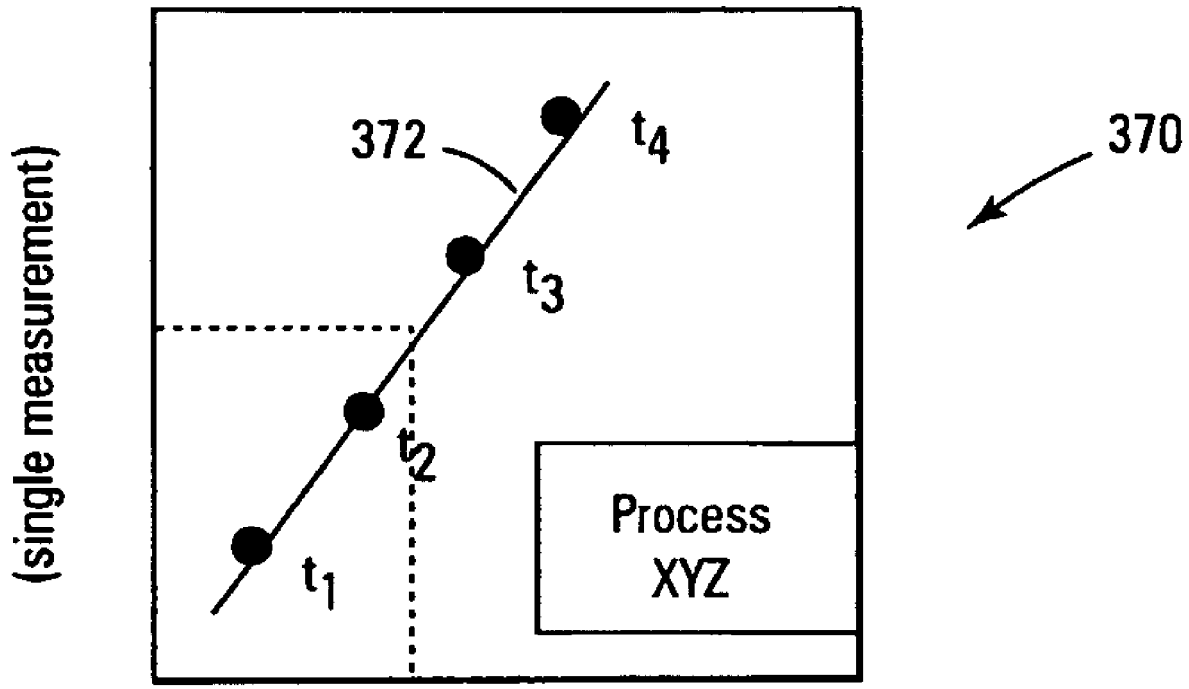
FIG. 12 is a graph for use in describing the correlation information shown generally in FIG. 9 according to the present invention.

For example, FIG. 12 is a graph 370 for use in describing illustrative calibration information, e.g., a calibration curve 372, generated for gate oxide layers. The graph 370 is representative of single non-invasive surface spectrum measurements collected for gate oxide layers of a plurality of samples (y-axis) and depth profile information representative of a total dose or concentration of a component (in this case, nitrogen) for the gate oxide layers of the plurality of samples (x-axis). For example, the concentration of a component for the gate oxide layers may be generated by integrating concentration of the component through the depth of the depth profile, e.g., summing depth profile data generated at each of the progressively deeper depths of the gate oxide layer.

The process conditions XYZ are the same for formation of all the gate oxide layers of the plurality of samples, except for the processing time used to dope the gate oxide layer with nitrogen. In other words, doping time was varied (e.g., $t_1$, $t_2$, $t_3$, etc.). Therefore, graph 370, e.g., the calibration curve 372, is representative of the relationship of non-invasive surface spectrum measurements for the samples and the total nitrogen concentration when various nitrogen doping time periods are used.

It will be recognized that the non-invasive surface spectrum measurements and the depth profiling performed with respect to the gate oxide layers of the samples must be consistent from sample to sample. In other words, such processes must be carried out under the same set of parameters.

The generation of depth profile information may be carried out in any known manner. However, preferably, the methods and systems previously described herein with reference to FIGS. 1-8 are used. For example, preferably, the depth profile data is generated using one or more of a high analyzer angle, a low ion angle for removal of material, low energy ions for removing material, and a differential profile depth correction algorithm as described therein and herein previously with reference to FIGS. 1-8.

However, as indicated above, other depth profiling methods and systems may be used. For example, ESCA depth profiling using a low analyzer angle may be used to provide the depth profile information, as well as SIMS, AES, TEM, or other surface analysis techniques.

Depth profile information as used herein may refer any information collected, analyzed, combined, or otherwise based on data collected using invasive depth profiling techniques. For example, such depth profile information may refer to individual depth profile data used to describe a characteristic of a sample at a particular depth, or may refer to information representative of a characteristic of the sample along its depth, e.g., concentration of a component through the depth of a thin film, thickness of the film, etc. For example, as described above, concentration of a component for the gate oxide layer may be generated by integrating concentration of the component through the depth of the depth profile, e.g., summing depth profile data generated at each of the progressively deeper depths of the gate oxide layer. Such concentration may be referred to as depth profile information.

Figure 11:
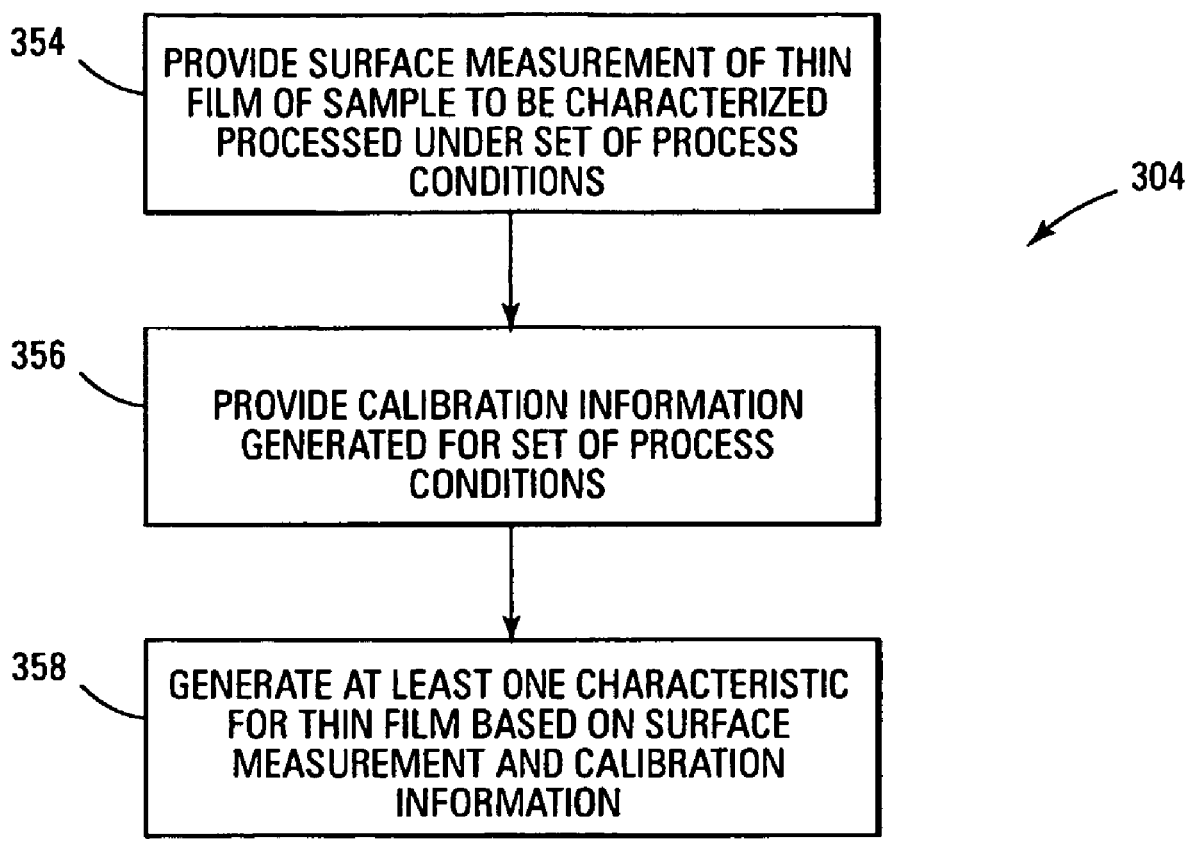
FIG. 11 is a more detailed flow diagram of one illustrative embodiment of a method for using the calibration information according to the present invention as generally shown in FIG. 9.

FIG. 11 shows a more detailed flow diagram of one illustrative embodiment of a method 304 for using the calibration information generated employing one or more features described above. As shown in block 354, non-invasive surface spectrum measurements of a sample to be characterized, e.g., a thin film, are provided. The sample to be characterized is formed using the same process conditions as the plurality of samples used to generate the calibration information. Further, the non-invasive surface spectrum measurements are preferably performed under the same set of parameters used to collect information to generate the calibration information. In addition to providing non-invasive surface spectrum measurements of the sample to be characterized, calibration information generated using the plurality of samples is also provided (block 356).

Thereafter, at least one characteristic of the sample (e.g., concentration of a thin film of the sample, thickness of the thin film, etc.) is generated based on the non-invasive surface spectrum measurements of the sample to be characterized and the calibration information (block 358). In other words, with surface spectrum measurements of the plurality of samples being correlated with the depth profile information for the plurality of samples, one or more characteristics corresponding to the depth profile information for a particular surface measurement are equally applicable to the sample to be characterized which has such particular surface measurement.

For example, a surface measurement is taken for a gate oxide layer to be analyzed. The surface spectrum measurements of the gate oxide layer to be analyzed may be compared to surface spectrum measurements of the plurality of samples used in generating the calibration information, e.g., concentration of nitrogen of the gate oxide layer corresponding to certain surface spectrum measurements. The concentration of nitrogen for the gate oxide layer being analyzed can be equated to the nitrogen concentration corresponding to the surface measurement of the plurality of samples that is comparable to the non-invasive surface spectrum measurements of the gate oxide being analyzed.

One skilled in the art will recognize that the processes described with reference to FIGS. 9-12, and also others described below with reference to FIGS. 13-15, can be implemented using the analysis system 1 described herein with modification to provide suitable processing capabilities. The analysis system may incorporate the systems previously described herein available from Physical Electronics, Inc. Further, the analysis system may be a standalone tool or the system may be interfaced to a device processing tool, e.g., a fabrication tool, such as a part of a cluster tool used in formation of gate oxides. The analysis system or tool is able to provide the calibration information and also be used to perform the analysis using the calibration information.

Further, one skilled in the art will recognize that the non-invasive characterization of the sample may be performed for a small portion of a sample, e.g., analysis of a spot, or may be performed for a larger region of a sample, e.g., a wafer or disc media. Such a large area analysis may be accomplished through rastering as previously described herein with respect to depth profiling.

The present non-invasive characterization method is particularly beneficial in analysis of thin films, preferably thin dielectric films, and more preferably nitrided silicon oxide films as shall be described with reference to FIGS. 13-15. For example, in illustrative formation processes for a nitrided silicon oxide film, the film may be formed by using nitrogen plasma, or an ion beam, to incorporate nitrogen into an oxide film, or, the nitrogen may be incorporated as the oxide is grown. The present invention is not limited to any particular method of providing the film or providing a sample including the film.

Figure 13:
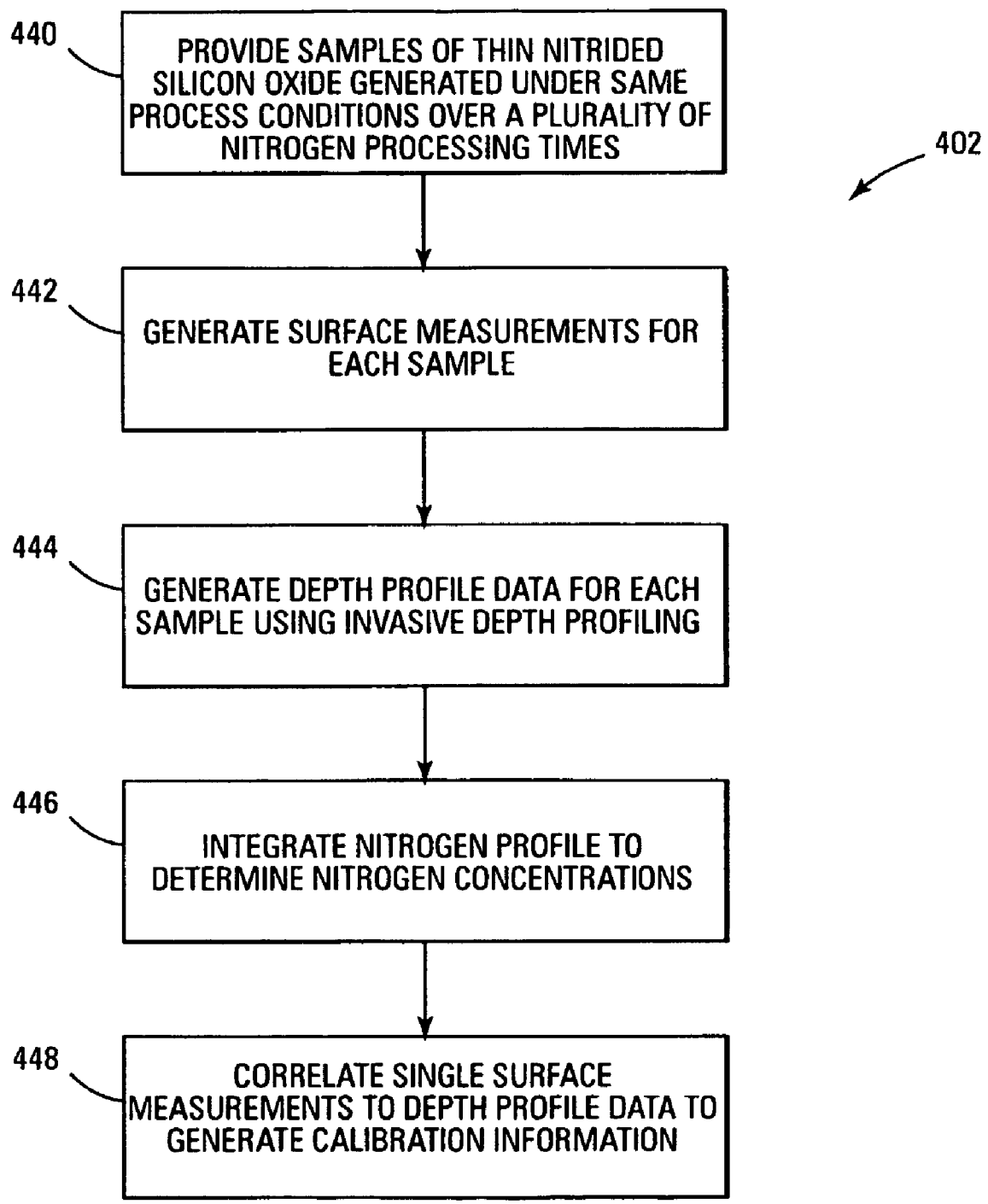
FIG. 13 is a more detailed flow diagram of one illustrative embodiment of a method for generating calibration information for nitrided silicon oxide films according to the present invention.

FIG. 13 shows one illustrative process 402 for generating calibration information for use in analysis of a thin nitrided silicon oxide film. FIG. 14 shows one illustrative embodiment of a method 450 for using such calibration information for non-invasive analysis of the thin nitrided silicon oxide film.

Figure 14:
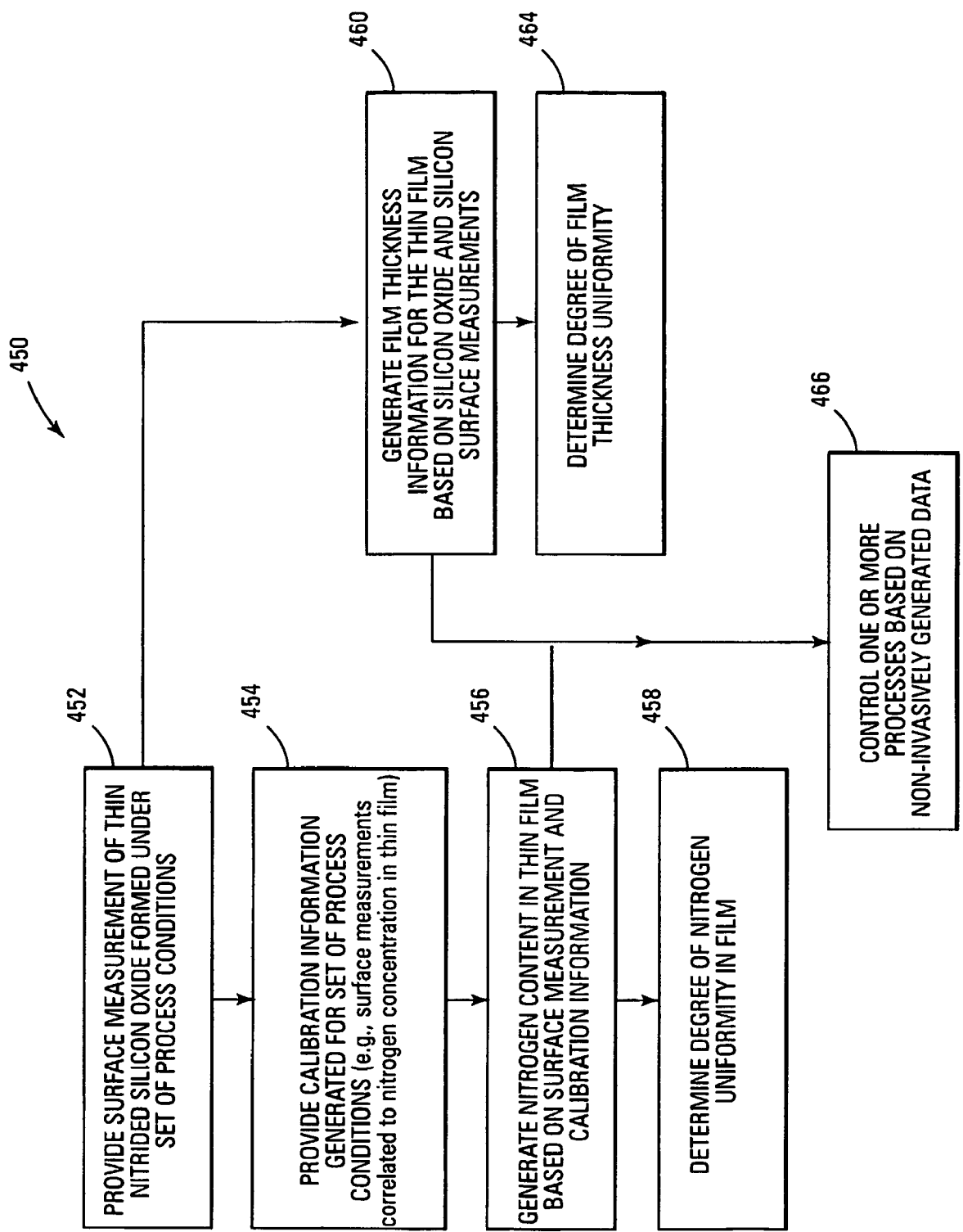
FIG. 14 is a more detailed flow diagram of one illustrative embodiment of a method for using calibration information to characterize a nitrided silicon oxide film according to the present invention.

To generate the calibration information as shown in FIG. 14, a plurality of thin nitrided silicon oxide films, e.g., thin films formed on a substrate, are provided (block 440). Each of the plurality of thin nitrided silicon oxide films is formed under the same process conditions.

Surface spectrum measurements are collected for each nitrided silicon oxide film (block 442). Further, depth profile information is generated for each thin nitrided silicon oxide film using invasive depth profiling techniques (block 444). The single surface spectrum measurements for such samples can be correlated to the depth profile information to generate calibration information (block 448).

Figure 15:
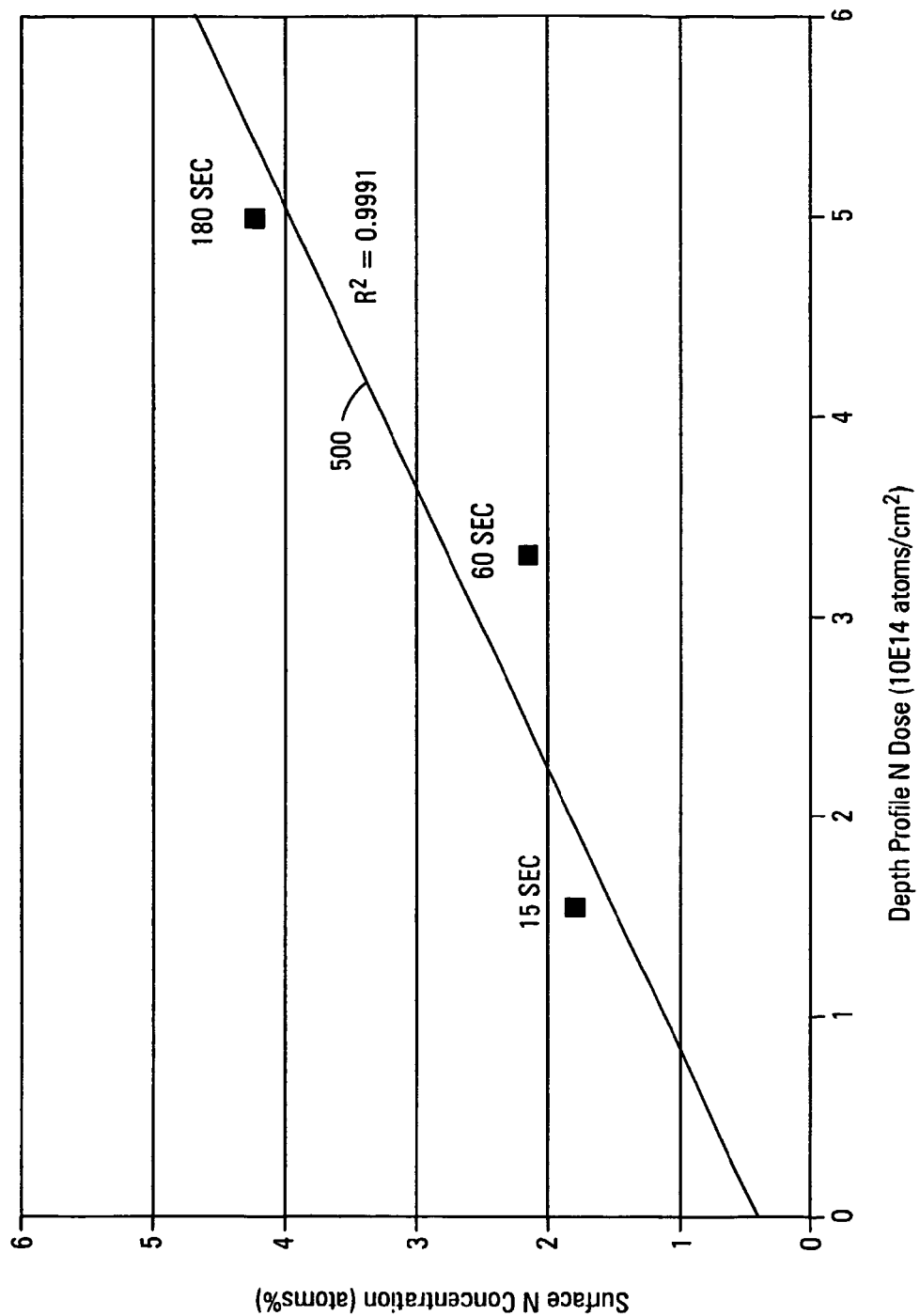
FIG. 15 is a graph for use in describing illustrative correlation information for a nitrided silicon oxide film according to the present invention.

For example, FIG. 15 is a graph 490 for use in describing illustrative calibration information, e.g., a calibration curve 500, generated for a thin nitrided silicon oxide film. The graph 490 is representative of single non-invasive surface spectrum measurements collected for nitrided silicon oxide layers of a plurality of samples (y-axis) and depth profile information representative of a total dose or concentration of nitrogen for the nitrided silicon oxide layers of the plurality of samples (x-axis). In this particular embodiment, the concentration of nitrogen for the nitrided silicon oxide layers may be generated by integrating concentration of nitrogen in the entire depth profile of the film, e.g., summing depth profile data representative of the nitrogen concentration generated at each of the progressively deeper depths of the nitrided silicon oxide layer (block 446).

The process conditions are the same for the formation of all the nitrided silicon oxide layers of the plurality of samples, except for the processing time used to dope the silicon oxide layer with nitrogen. In other words, doping time is varied as shown in the graph 490 by the times 15 seconds, 60 seconds, and 180 seconds. Therefore, graph 490, e.g., the calibration curve 500, is representative of the relationship of non-invasive surface spectrum measurements representative of the concentration of nitrogen and the total nitrogen concentration represented by the depth profile data when various nitrogen doping time periods are used. "R" squared as shown on the graph is the linear correlation coefficient indicative of the linearity of the plotted data.

It will be recognized that the non-invasive surface spectrum measurements and the depth profiling performed with respect to the nitrided silicon oxide layers of the samples must be consistent from sample to sample. In other words, such processes must be carried out under the same set of parameters.

FIG. 14 shows a flow diagram of an illustrative embodiment of a method 450 for using the calibration information generated for the thin nitrided silicon oxide films describe above. As shown in block 452, non-invasive surface spectrum measurements of a nitrided silicon oxide film to be characterized are provided. The nitrided silicon oxide film to be characterized is formed using the same process conditions as the plurality of thin nitrided silicon oxide films used to generate the calibration information. Further, the non-invasive surface spectrum measurements are preferably performed under the same set of parameters used to collect information to generate the calibration information. In addition to providing non-invasive surface spectrum measurements of the thin nitrided silicon oxide film to be characterized, the calibration information generated using the plurality of thin nitrided silicon oxide is also provided (block 454).

Thereafter, nitrogen content in the thin nitrided silicon oxide film at a spot is generated based on the non-invasive surface spectrum measurements of the film to be characterized and the calibration information (block 456). In other words, with surface spectrum measurements of the plurality of nitrided silicon oxide films being correlated with the depth profile information for such films, the nitrogen concentration corresponding to the depth profile information for a particular surface measurement are equally applicable to the thin nitrided silicon oxide film to be characterized which has the particular surface measurement.

Further, in addition to determining the nitrogen at a spot of the thin nitrided silicon oxide film, rastering or scanning of the x-ray beam can be used to provide measurements from a relatively larger spot region, e.g., (1.5 mm)$^2$ while the sample can be moved to provide measurements over an larger area, e.g., a wafer, disc media, etc. As such, nitrogen content can be determined for the larger area across the thin film. With the nitrogen content known, the degree of nitrogen uniformity in the nitrided film can be determined, e.g., uniformity of nitrogen distribution across a wafer having the film to be analyzed formed thereon (block 458).

The surface spectrum measurements performed on the nitrided silicon oxide film to be characterized (block 452), can also be used to determine thickness of the thin film (block 460). For example, the silicon oxide and silicon elemental spectrum measurements may be used to determine thickness as is known to one skilled in the art. Such analysis is described in Briggs, D. and Seah M. P., *Practical Surface Analysis*, 2$^{nd}$ Ed., Vol. 1, Auger and X-ray Photoelectron Spectroscopy, Sec. 5.4.2, pp. 244-248, John Wiley & Sons, Ltd. (July 1995). As such, using the same surface spectrum measurements, thickness and nitrogen content can be determined.

With the film thickness being determined as generally shown by block 46, sample motion can be used to cover a much larger area, e.g., obtain measurements from a larger area. In other words, thickness of the film can be determined for the larger area across the thin film. With the thickness known, the degree of uniformity in the thickness across the nitrided silicon oxide film can be determined (block 464), e.g., uniformity of thickness of the film across a wafer can be determined.

As shown generally by block 466, with various characteristics of the nitrided silicon oxide film being generated non-invasively, one or more processes can be controlled based thereon. For example, as previously described herein, the analysis system can be interfaced to production tools used to fabricate the nitrided silicon oxide films. The calibration can be repeated and optimized for specific gate oxide processes and/or equipment operation conditions.

All patents and references disclosed herein are incorporated by reference in their entirety, as if individually incorporated. The preceding specific embodiments are illustrative of the practice of the present invention. It is to be understood, therefore, that other expedients known to those skilled in the art or disclosed herein may be employed without departing from the invention or the scope of the appended claims.

What is claimed is:

1. A method for use in characterizing a sample, wherein the method comprises:

collecting depth profile data at each of a plurality of depths of the sample, each depth corresponding to a sample surface, wherein one or more of the plurality of depths of the sample are provided by removing material from the sample during material removal intervals resulting in sample surfaces at the one or more depths of the sample, and further wherein collecting depth profile data at each of the plurality of depths of the sample comprises:

irradiating the sample with x-rays resulting in the escape of photoelectrons therefrom;

detecting photoelectrons escaping from the sample, wherein detecting the photoelectrons comprises providing an analyzer comprising an input lens receptive of photoelectrons, the input lens having a central axis extending therethrough, and positioning the input lens such that the central axis of the input lens is at an analyzer angle relative to the sample surface in a range of about 45 degrees to about 90 degrees; and generating a signal representative of the detected photoelectrons;

using the depth profile data collected for a first and second depth to characterize the sample at the first depth, wherein the second depth is at a position deeper in the sample than the first depth, and wherein characterizing the sample at the first depth comprises removing the depth profile data collected for the second depth from the depth profile data collected for the first depth; and using the depth profile data collected for the first and second depth to calibrate the depth profile of a second sample, wherein the depth profile of the second sample is collected non-invasively.

2. The method of claim 1, wherein the second depth is a depth at a sample surface resulting from removal of material from the sample during a material removal interval immediately following collection of depth profile data at the first depth.

3. The method of claim 1, wherein the analyzer angle is in the range of about 60 degrees to about 90 degrees.

4. The method of claim 1, wherein the input lens is receptive to photoelectrons having a photoelectron take-off angle that falls in a cone of +/−20 degrees centered at the analyzer angle.

5. The method of claim 1, wherein removing material from the sample during material removal intervals comprises sputtering material from the sample using ions having ion energies of less than 500 eV.

6. The method of claim 1, wherein removing material from the sample during material removal intervals comprises sputtering material from a surface of the sample using an ion beam provided at an ion angle less than or equal to about 45 degrees relative to the sample surface.

7. The method of claim 6, wherein using the ion beam comprises providing the ion beam at an ion angle less than or equal to about 20 degrees relative to the sample surface.

8. The method of claim 1, wherein the sample comprises a film having a thickness of less than about 10 nanometers.

9. The method of claim 8, wherein the film comprises a gate dielectric film.

10. The method of claim 1, wherein removing material from the sample during material removal intervals comprises sputtering material from the sample using an ion beam comprising ions heavier than argon ions.

11. The method of claim 1, wherein using the depth profile data collected for the first and second depths to characterize the sample at the first depth comprises:
obtaining measured peak areas for at least one component from the depth profile data collected at the first depth, wherein the measured peak areas are representative of concentration contributions from a surface layer and also deeper layers of the sample,
wherein the concentration contributions of the deeper layers are represented by the depth profile data collected at the second depth;
determining calculated peak areas for the at least one component corresponding to a measure of that component's concentration in the surface layer by removing concentration contributions of the deeper layers from the measured peak areas; and
converting the calculated peak areas into at least concentration of the at least one component at the first depth.

12. The method of claim 1, wherein using the depth profile data collected for the first and second depths to characterize the sample at the first depth further comprises using depth profile data collected for a plurality of additional depths to characterize a certain thickness of the sample.

13. A method for use in characterizing a sample, wherein the method comprises:
collecting depth profile data at each of a plurality of depths of the sample, each depth having a corresponding sample surface, wherein one or more of the plurality of depths of the sample are provided by removing material from the sample during material removal intervals resulting in sample surfaces at the one or more depths of the sample, wherein collecting depth profile data at each of the plurality of depths of the sample comprises:
irradiating the sample with x-rays resulting in the escape of photoelectrons therefrom; and
detecting photoelectrons escaping from the sample, wherein detecting photoelectrons escaping from the sample comprises:
providing an analyzer comprising an input lens receptive of photoelectrons, the input lens having a central axis extending therethrough; and
positioning the input lens such that the central axis of the input lens is at an analyzer angle relative to the sample surface, wherein the analyzer angle is in the range of about 45 degrees to about 90 degrees;
operating on the depth profile data to provide characterization of the sample at each of one or more of the plurality of depths thereof wherein operating on the depth profile data comprises:
obtaining measured peak areas for at least one component from the depth profile data collected at a particular depth, wherein the measured peak areas are representative of concentration contributions from a surface layer corresponding to the particular depth and also deeper layers of the sample;
determining calculated peak areas for the at least one component corresponding to a measure of that component's concentration in the surface layer by removing concentration contributions of the deeper layers from the measured peak areas; and
converting the calculated peak areas into at least concentration of the at least one component at the particular depth; and using the concentration of the one component to calibrate the depth profile of a second sample, wherein the depth profile of the second sample is collected non-invasively 14. The method of claim 13, wherein the sample comprises a film having a thickness of less than about 10 nanometers.

15. The method of claim 14, wherein the film comprises a gate dielectric film.

16. A method for use in characterizing a sample, wherein the method comprises:
collecting depth profile data at a first depth of a sample, wherein collecting depth profile data at the first depth of the sample comprises:
irradiating the sample with x-rays resulting in the escape of photoelectrons therefrom;
detecting photoelectrons escaping from the sample, wherein detecting photoelectrons escaping from the sample comprises providing an analyzer comprising an input lens receptive of photoelectrons, the input lens having a central axis extending therethrough, and positioning the input lens such that the central axis of the input lens is at an analyzer angle relative to the sample surface, wherein the analyzer angle is in the range of about 45 degrees to about 90 degrees; and
generating a signal representative of the detected photoelectrons; removing material from the sample exposing a second depth of the sample, wherein removing material from the sample during material removal intervals comprises sputtering material from a surface of the sample using an ion beam provided at an ion angle less than or equal to about 45 degrees relative to the sample surface, and further wherein the ion beam comprises ions having ion energies of less than 500 eV;
collecting depth profile data at the second depth of the sample, wherein collecting depth profile data at the second depth of the sample comprises:
irradiating the sample with x-rays resulting in the escape of photoelectrons therefrom; detecting photoelectrons escaping from the sample using the input lens positioned at the analyzer angle; and
generating a signal representative of the detected photoelectrons;
using the depth profile data collected for the first and second depths to calculate concentration of components at the first depth, and wherein calculating the concentration of components at the first depth comprises removing the depth profile data collected for the second depth from the depth profile data collected for the first depth; and
using the depth profile data collected for the first and second depths to calibrate the depth profile of a second sample, wherein the depth profile of the second sample is collected non-invasively.

17. The method of claim 16, wherein the sample comprises a film having a thickness of less than about 10 nanometers.

18. A system for use in characterizing a sample, wherein the system comprises:

an x-ray source operable to irradiate the sample, when the sample is positioned at an analysis plane of the system, with x-rays resulting in the escape of photoelectrons therefrom;

an analyzer operable to detect photoelectrons escaping from the sample, wherein the analyzer comprises an input lens receptive of photoelectrons, the input lens having a central axis extending therethrough, wherein the input lens is positioned such that the central axis of the input lens is at an analyzer angle relative to the analysis plane, wherein the analyzer angle is in the range of about 45 degrees to about 90 degrees, and further wherein the analyzer is operable to generate a signal representative of the detected photoelectrons;

an ion source operable to provide ions for removal of material from a sample positioned at the analysis plane during material removal intervals resulting in sample surfaces at one or more depths of the sample; and a computing apparatus operable to generate depth profile data based on the signals representative of the detected photoelectrons for each of a plurality of depths of the sample, further operable to use the depth profile data collected for a first and second depth to characterize the sample at the first depth, wherein the second depth is at a position deeper in the sample than the first depth, and wherein characterizing the sample at the first depth comprises removing the depth profile data collected for the second depth from the depth profile data collected for the first depth, and further operable to use the depth profile data collected for the first and second depth to calibrate the depth profile of a second sample, wherein the depth profile of the second sample is collected non-invasively.

19. The system of claim 18, wherein the second depth is a depth at a sample surface resulting from removal of material from the sample during a material removal interval immediately following collection of depth profile data at the first depth.

20. The system of claim 18, wherein the analyzer angle is in the range of about 60 degrees to about 90 degrees.

21. The system of claim 18, wherein ions provided by the ion source have ion energies of less than 500 eV.

22. The system of claim 18, wherein the ion source is operable to provide an ion beam at an ion angle less than or equal to about 45 degrees relative to the analysis plane.

23. The system of claim 22, wherein the ion source is operable to provide an ion beam at an ion angle less than or equal to about 20 degrees relative to the analysis plane.

24. The system of claim 18, wherein ions provided by the ion source comprise ions heavier than argon ions.

25. The system of claim 18, wherein the computer apparatus is operable to use depth profile data collected for a plurality of additional depths to characterize a certain thickness of the sample.

26. A system for use in characterizing a sample, wherein the system comprises:

an x-ray source operable to irradiate the sample, when the sample is positioned at an analysis plane of the system, with x-rays resulting in the escape of photoelectrons therefrom;

an analyzer operable to detect photoelectrons escaping from the sample, wherein the analyzer comprises an input lens receptive of photoelectrons, the input lens having a central axis extending therethrough, wherein the input lens is positioned such that the central axis of the input lens is at an analyzer angle relative to the analysis plane, wherein the analyzer angle is in the range of about 45 degrees to about 90 degrees, and further wherein the analyzer is operable to generate a signal representative of the detected photoelectrons;

an ion source operable to provide ions for removal of material from the sample positioned at the analysis plane during material removal intervals resulting in sample surfaces at one or more depths of the sample, wherein the ion source is operable to provide an ion beam at an ion angle less than or equal to about 45 degrees relative to the analysis plane, the ion beam comprising ions having ion energies of less than 500 eV;

a computing apparatus operable to generate depth profile data based on the signals representative of the detected photoelectrons for each of a plurality of depths of the sample, further operable to use the depth profile data collected for a first and second depth to characterize the sample at the first depth, wherein the second depth is at a position deeper in the sample than the first depth, and wherein characterizing the sample at the first depth comprises removing the depth profile data collected for the second depth from the depth profile data collected for the first depth, and further operable to use the depth profile data collected for the first and second depth to calibrate the depth profile of a second sample, wherein the depth profile of the second sample is collected non-invasively.

27. The system of claim 26, wherein the analyzer angle is in the range of about 60 degrees to about 90 degrees.

28. The system of claim 26, wherein the ion source is operable to provide an ion beam at an ion angle less than or equal to about 20 degrees relative to the analysis plane.

29. The system of claim 26, wherein the computer apparatus is operable to use depth profile data collected for a plurality of additional depths to characterize a certain thickness of the sample.

30. A method for use in characterizing a sample, wherein the method comprises:

collecting depth profile data at each of a plurality of depths of the sample, each depth corresponding to a sample surface, wherein one or more of the plurality of depths of the sample are provided by removing material from the sample during material removal intervals resulting in sample surfaces at the one or more depths of the sample, and further wherein collecting depth profile data at each of the plurality of depths of the sample comprises:

irradiating the sample with x-rays resulting in the escape of photoelectrons therefrom;

detecting photoelectrons escaping from the sample, wherein detecting the photoelectrons comprises providing an analyzer comprising an input lens receptive of photoelectrons, the input lens having a central axis extending therethrough, wherein the input lens is receptive to photoelectrons having a photoelectron take-off angle that falls in a cone of +/-20 degrees centered at the analyzer angle; and generating a signal representative of the detected photoelectrons; and using the depth profile data collected for a first and second depth to characterize the sample at the first depth, wherein the second depth is at a position deeper in the sample than the first depth, wherein characterizing the sample at the first depth comprises removing the depth profile data collected for the second depth from the depth profile data collected for the first depth; and using the depth profile data collected for the first and second depth to calibrate the depth profile of a second sample, wherein the depth profile of the second sample is collected non-invasively.

31. The method of claim 30, wherein the second depth is a depth at a sample surface resulting from removal of material from the sample during a material removal interval immediately following collection of depth profile data at the first depth.

32. The method of claim 30, wherein removing material from the sample during material removal intervals comprises sputtering material from the sample using ions having ion energies of less than 500 eV.

33. The method of claim 1, wherein removing material from the sample during material removal intervals comprises sputtering material from a surface of the sample using an ion beam provided at an ion angle less than or equal to about 45degrees relative to the sample surface.

34. The method of claim 33, wherein using the ion beam comprises providing the ion beam at an ion angle less than or equal to about 20 degrees relative to the sample surface.

* * * * *